US008313437B1

(12) United States Patent
Suri

(10) Patent No.: US 8,313,437 B1
(45) Date of Patent: Nov. 20, 2012

(54) VASCULAR ULTRASOUND INTIMA-MEDIA THICKNESS (IMT) MEASUREMENT SYSTEM

(76) Inventor: Jasjit S. Suri, Roseville, CA (US)

( * ) Notice: Subject to any disclaimer, the term of this patent is extended or adjusted under 35 U.S.C. 154(b) by 267 days.

(21) Appl. No.: 12/802,431

(22) Filed: Jun. 7, 2010

(51) Int. Cl.
*A61B 8/00* (2006.01)
*G06K 9/00* (2006.01)
(52) U.S. Cl. ......... 600/443; 600/438; 600/465; 382/128
(58) Field of Classification Search .................. 600/437, 600/443, 465; 382/128
See application file for complete search history.

(56) References Cited

U.S. PATENT DOCUMENTS

| | | | |
|---|---|---|---|
| 5,343,867 A | 9/1994 | Shankar | |
| 5,734,739 A | 3/1998 | Sheehan et al. | |
| 6,132,373 A | 10/2000 | Ito et al. | |
| 6,251,072 B1 | 6/2001 | Ladak et al. | |
| 6,267,728 B1 | 7/2001 | Hayden | |
| 6,347,152 B1 | 2/2002 | Shinagawa et al. | |
| 6,597,937 B2 | 7/2003 | Liu et al. | |
| 6,614,453 B1 | 9/2003 | Suri et al. | |
| 6,718,055 B1 | 4/2004 | Suri | |
| 6,785,409 B1 | 8/2004 | Suri | |
| 6,813,373 B1 | 11/2004 | Suri et al. | |
| 6,817,982 B2 | 11/2004 | Fritz et al. | |
| 6,835,177 B2 | 12/2004 | Fritz et al. | |
| 6,842,638 B1 | 1/2005 | Suri et al. | |
| 6,845,260 B2 | 1/2005 | Liu et al. | |
| 6,987,568 B2 | 1/2006 | Dana | |
| 7,020,314 B1 | 3/2006 | Suri et al. | |
| 7,024,027 B1 | 4/2006 | Suri et al. | |
| 7,074,187 B2 | 7/2006 | Selzer et al. | |
| 7,090,640 B2 * | 8/2006 | Barth et al. | .................. 600/443 |
| 7,110,000 B2 | 9/2006 | Zhang et al. | |
| 7,149,368 B2 | 12/2006 | Tong et al. | |
| 7,161,601 B2 | 1/2007 | Zhang et al. | |
| 7,272,241 B2 | 9/2007 | Demi et al. | |

(Continued)

FOREIGN PATENT DOCUMENTS

WO    WO03042921 A    5/2003

OTHER PUBLICATIONS

Gutierrez, Marco et al. "Assessment of carotid diameter and wall thickness in ultrasound images using active contours improved by a multiresolution techique". Medical Imaging 2002: Physiology and Function from Multidimensional Images, Proceedings of SPIE vol. 4683 (2002).*

(Continued)

*Primary Examiner* — Long V. Le
*Assistant Examiner* — Helene Bor
(74) *Attorney, Agent, or Firm* — Salter IP Law; Jim H. Salter

(57) ABSTRACT

A computer-implemented system and method for fast, reliable and automated processing for intima-media thickness (IMT) measurements. Various embodiments include receiving biomedical imaging data and patient demographic data corresponding to a current scan of a patient; checking the biomedical imaging data in real-time to determine if an artery of the patient has a calcium deposit in a proximal wall of the artery; acquiring arterial data of the patient as a combination of longitudinal B-mode and transverse B-mode data; using a data processor to automatically recognize the artery; using the data processor to calibrate a region of interest around the automatically recognized artery; and determining the intima-media thickness (IMT) of an arterial wall of the automatically recognized artery.

14 Claims, 30 Drawing Sheets

U.S. PATENT DOCUMENTS

| | | |
|---|---|---|
| 7,340,083 B2 | 3/2008 | Yuan et al. |
| 7,353,117 B2 | 4/2008 | Yuan et al. |
| 7,376,253 B2 | 5/2008 | Spreeuwers et al. |
| 7,639,261 B2 | 12/2009 | Sekine et al. |
| 7,657,299 B2 | 2/2010 | Huizenga et al. |
| 7,680,330 B2 | 3/2010 | Leung |
| 7,686,764 B2 * | 3/2010 | Watanabe et al. ............. 600/443 |
| 2003/0053669 A1 | 3/2003 | Suri et al. |
| 2003/0236460 A1 | 12/2003 | Ma et al. |
| 2004/0116808 A1 * | 6/2004 | Fritz et al. .................... 600/437 |
| 2004/0243365 A1 | 12/2004 | Yuan et al. |
| 2005/0042222 A1 | 2/2005 | Yamamoto et al. |
| 2005/0043614 A1 | 2/2005 | Huizenga et al. |
| 2005/0119555 A1 | 6/2005 | Fritz et al. |
| 2005/0267365 A1 * | 12/2005 | Sokulin et al. ................ 600/437 |
| 2006/0064016 A1 | 3/2006 | Demi et al. |
| 2006/0241465 A1 | 10/2006 | Huennekens et al. |
| 2007/0003116 A1 | 1/2007 | Yuan et al. |
| 2007/0038061 A1 | 2/2007 | Huennekens et al. |
| 2007/0269086 A1 | 11/2007 | Kerwin et al. |
| 2007/0287897 A1 | 12/2007 | Faris |
| 2008/0009702 A1 | 1/2008 | Liu et al. |
| 2008/0051658 A1 | 2/2008 | Demi et al. |
| 2008/0080755 A1 | 4/2008 | Payonk et al. |
| 2008/0095422 A1 | 4/2008 | Suri et al. |
| 2008/0145841 A1 | 6/2008 | Libutti et al. |
| 2008/0171939 A1 | 7/2008 | Ishihara |
| 2008/0221446 A1 | 9/2008 | Washburn et al. |
| 2008/0269595 A1 | 10/2008 | Wong |
| 2008/0274457 A1 | 11/2008 | Eng et al. |
| 2008/0316374 A1 | 12/2008 | Koike et al. |
| 2009/0028793 A1 | 1/2009 | Neri et al. |
| 2009/0252395 A1 | 10/2009 | Chan et al. |
| 2010/0060644 A1 | 3/2010 | Elie et al. |
| 2010/0081931 A1 | 4/2010 | Destrempes et al. |

* cited by examiner

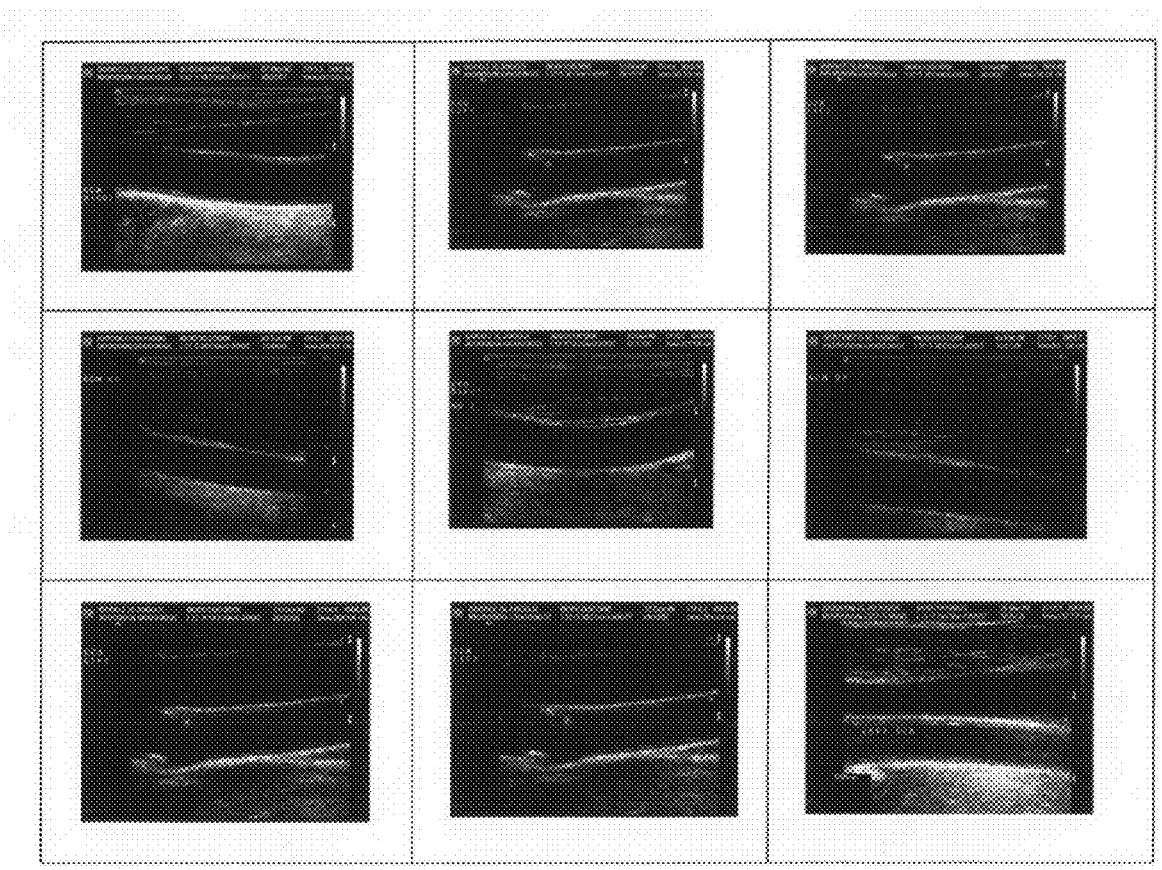
FIGURE 16A (Original DICOM Images)

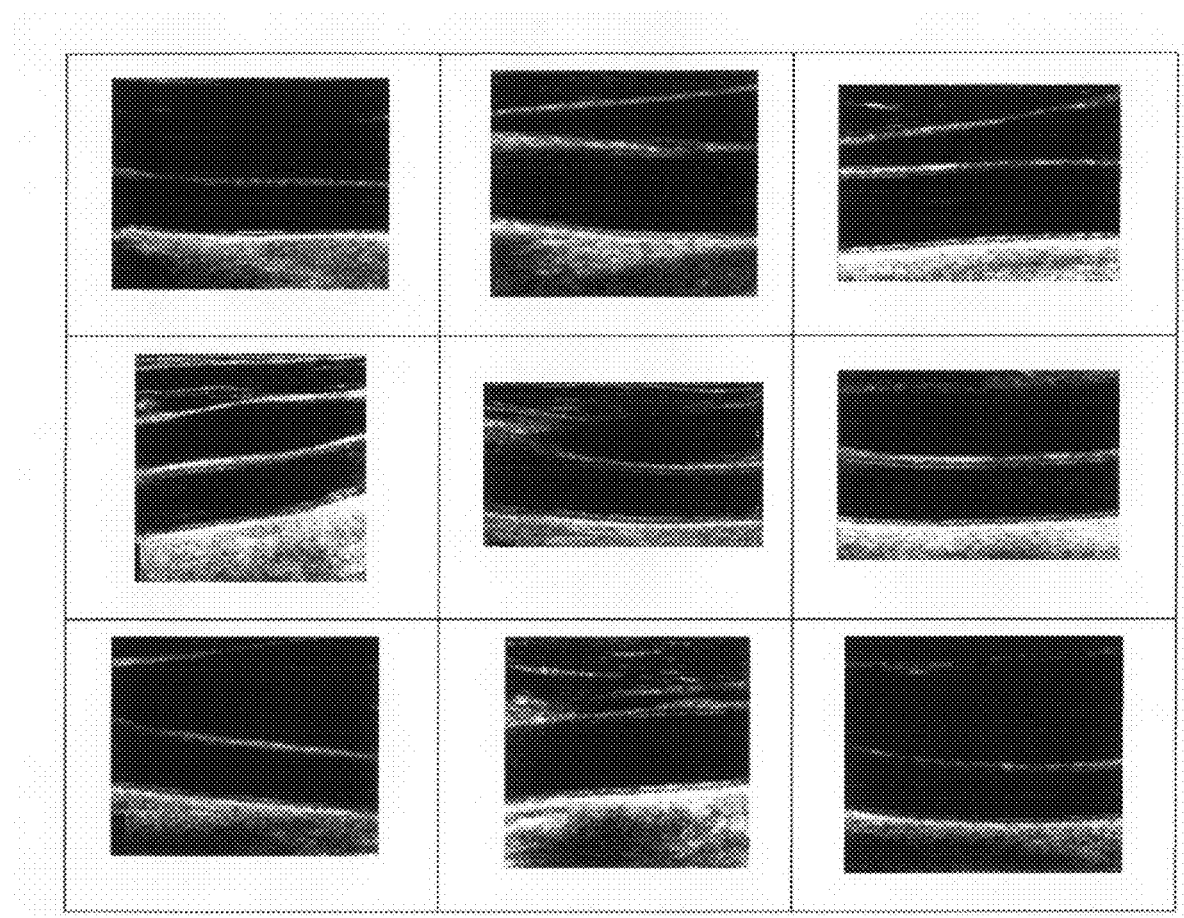
FIGURE 16B (Cropped Images)

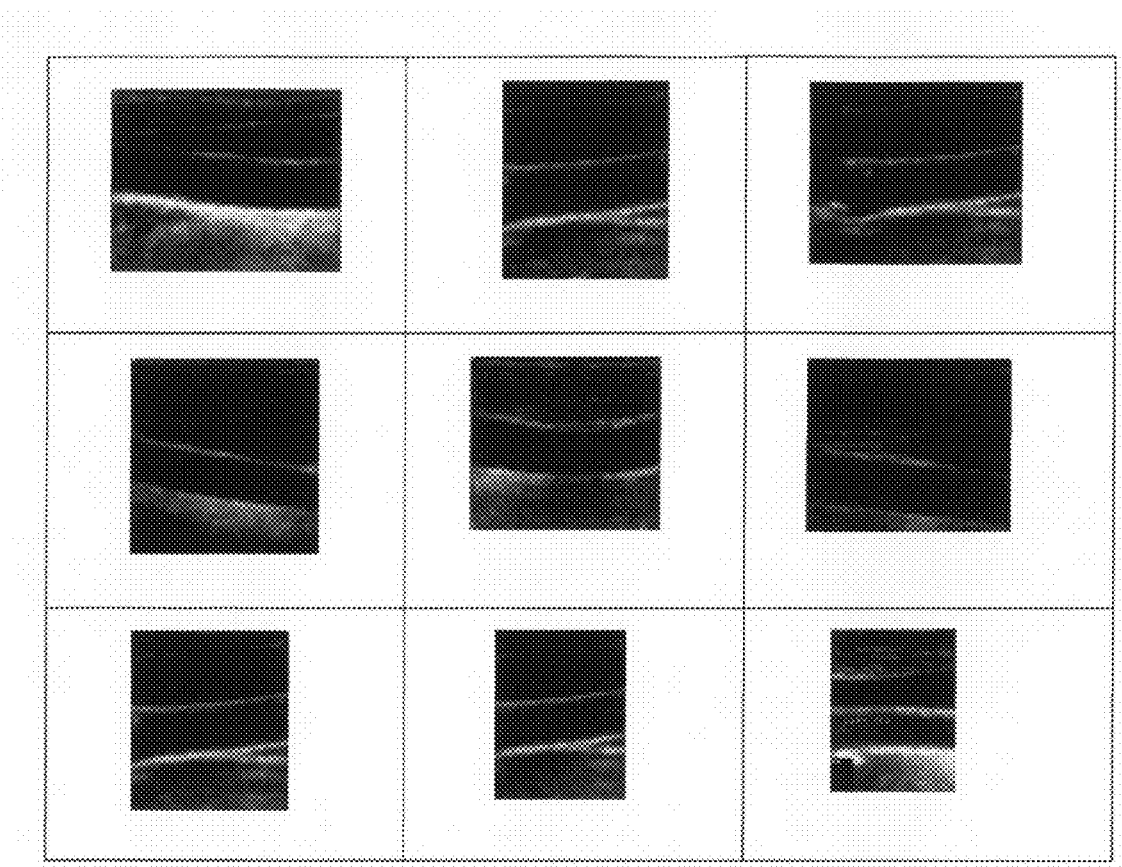
FIGURE 16C (Down Sampled Images)

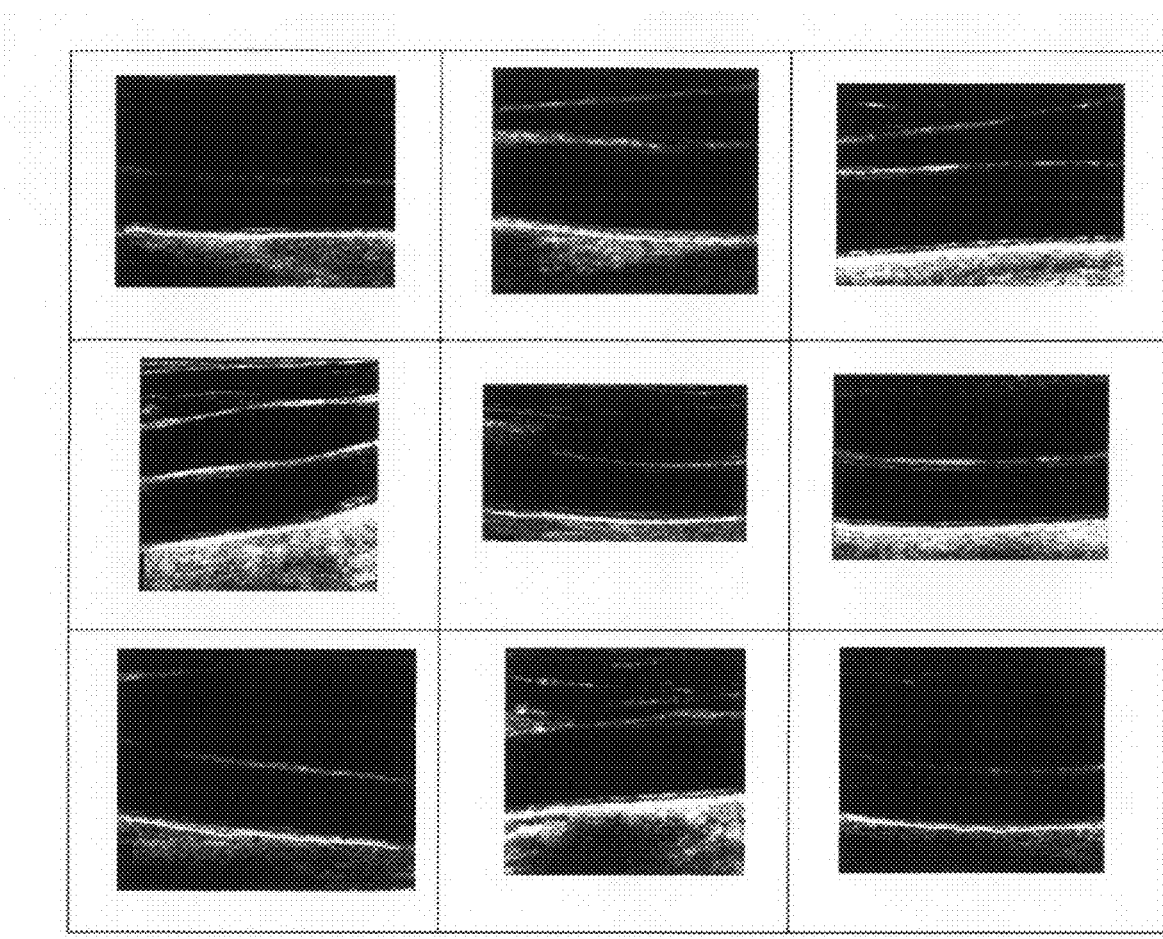
FIGURE 17 (Recognition Phase of Adventitia)

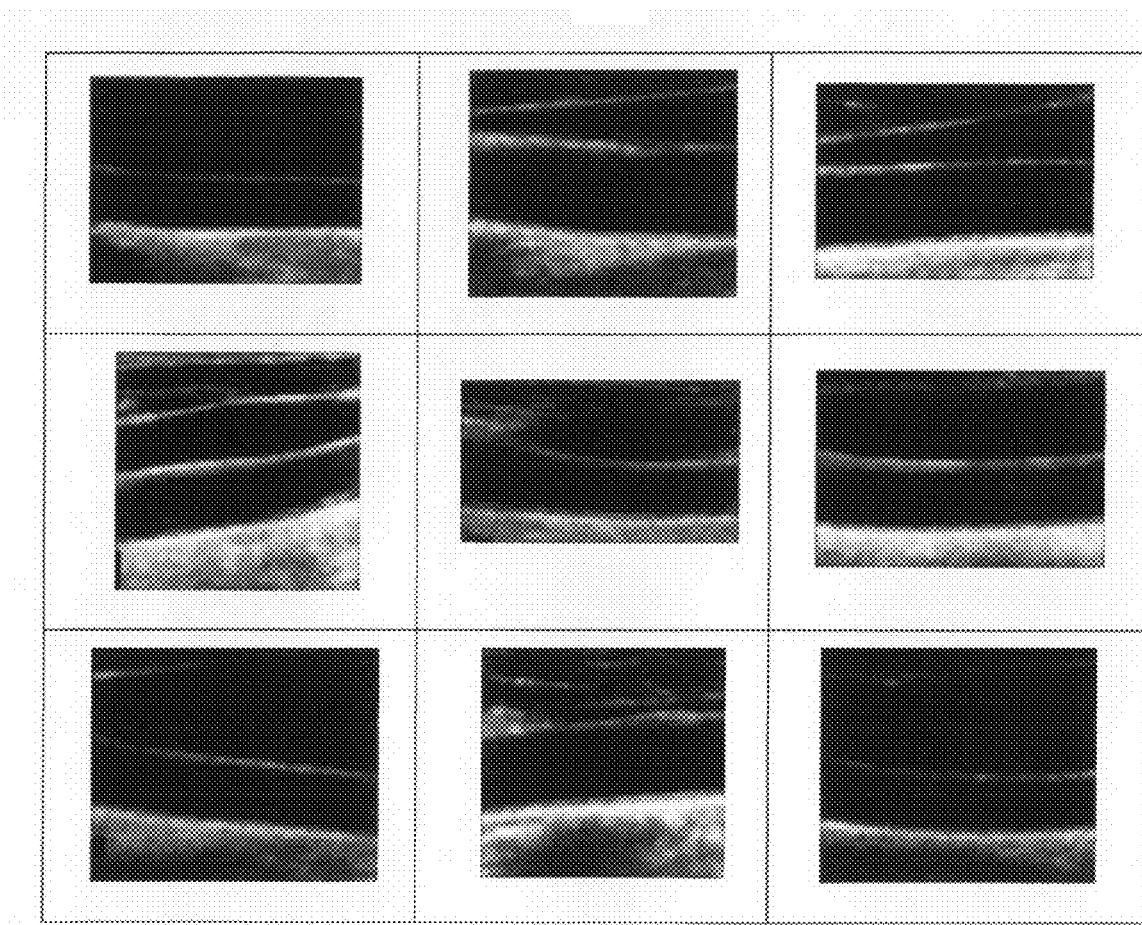
FIGURE 18A (Despeckle Filtering)

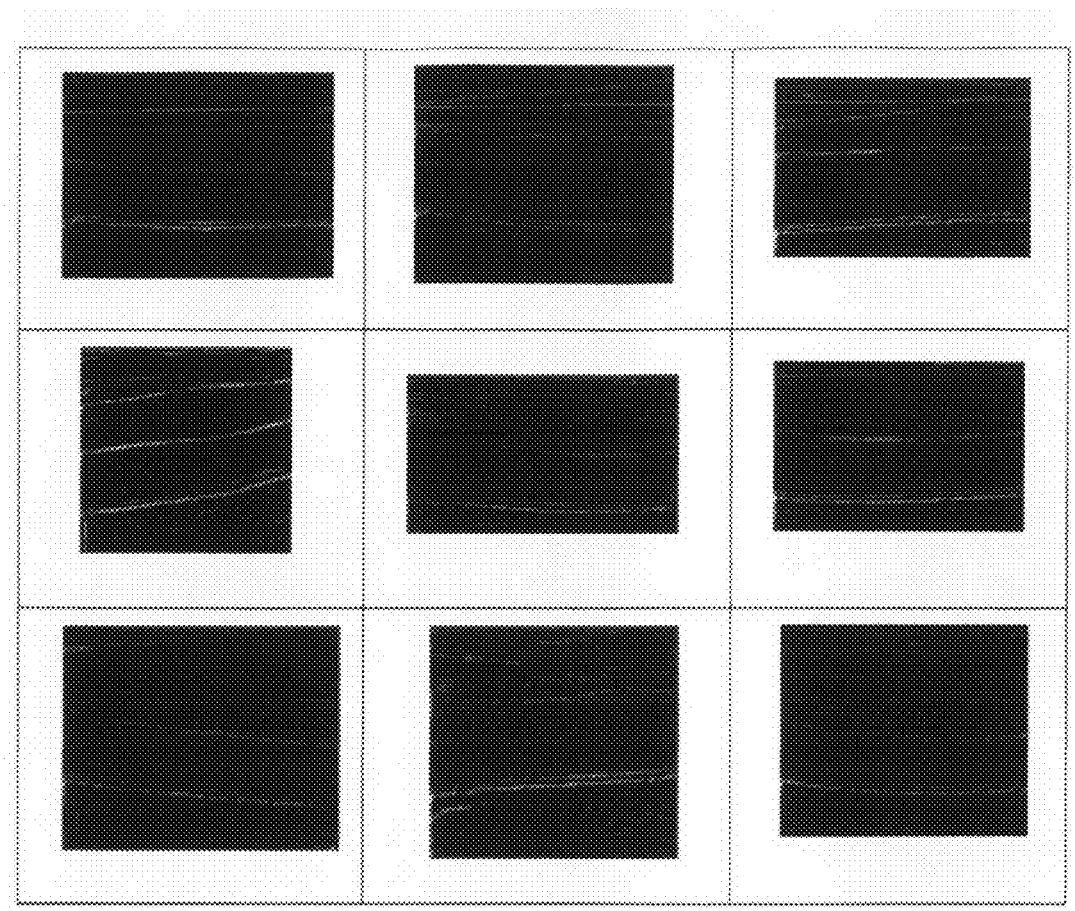
FIGURE 19 (Calibration Stage)

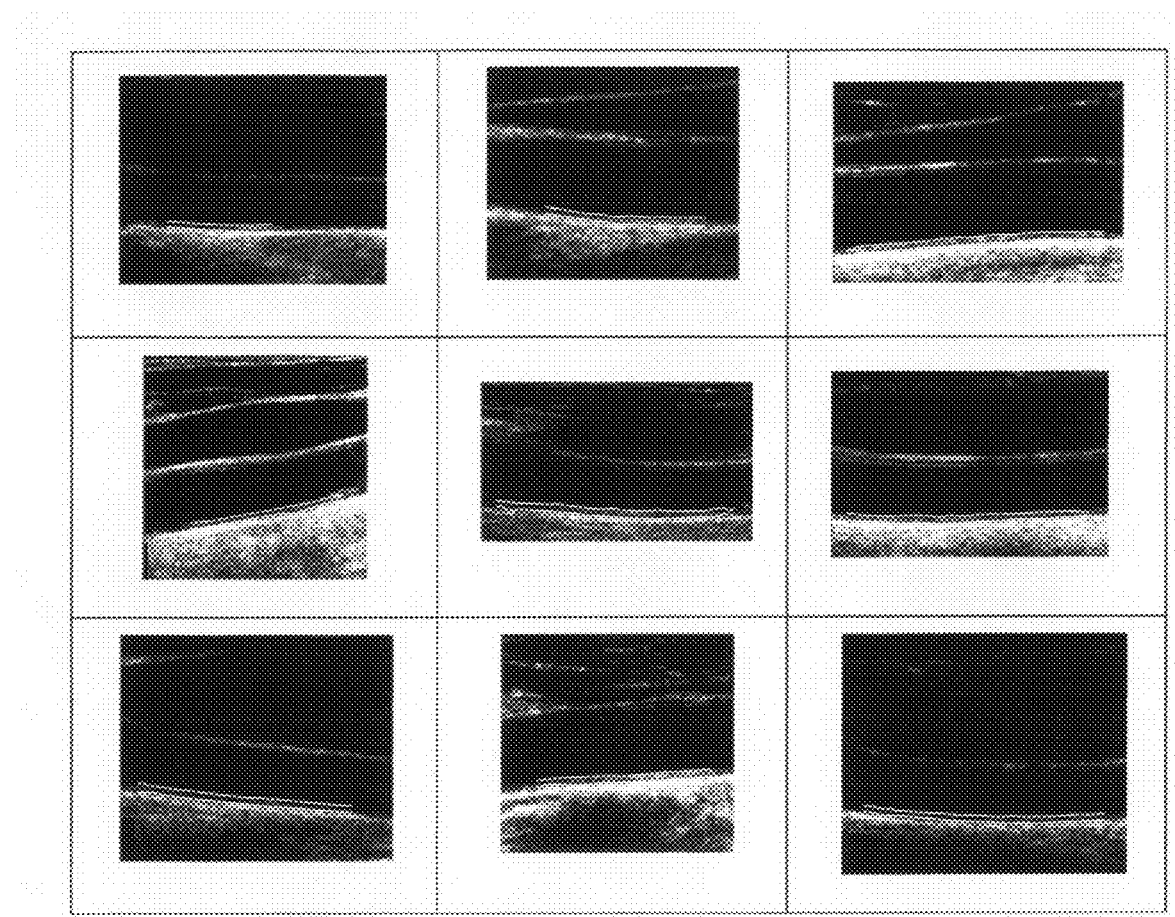
FIGURE 20 (LIMA Border Segmentation)

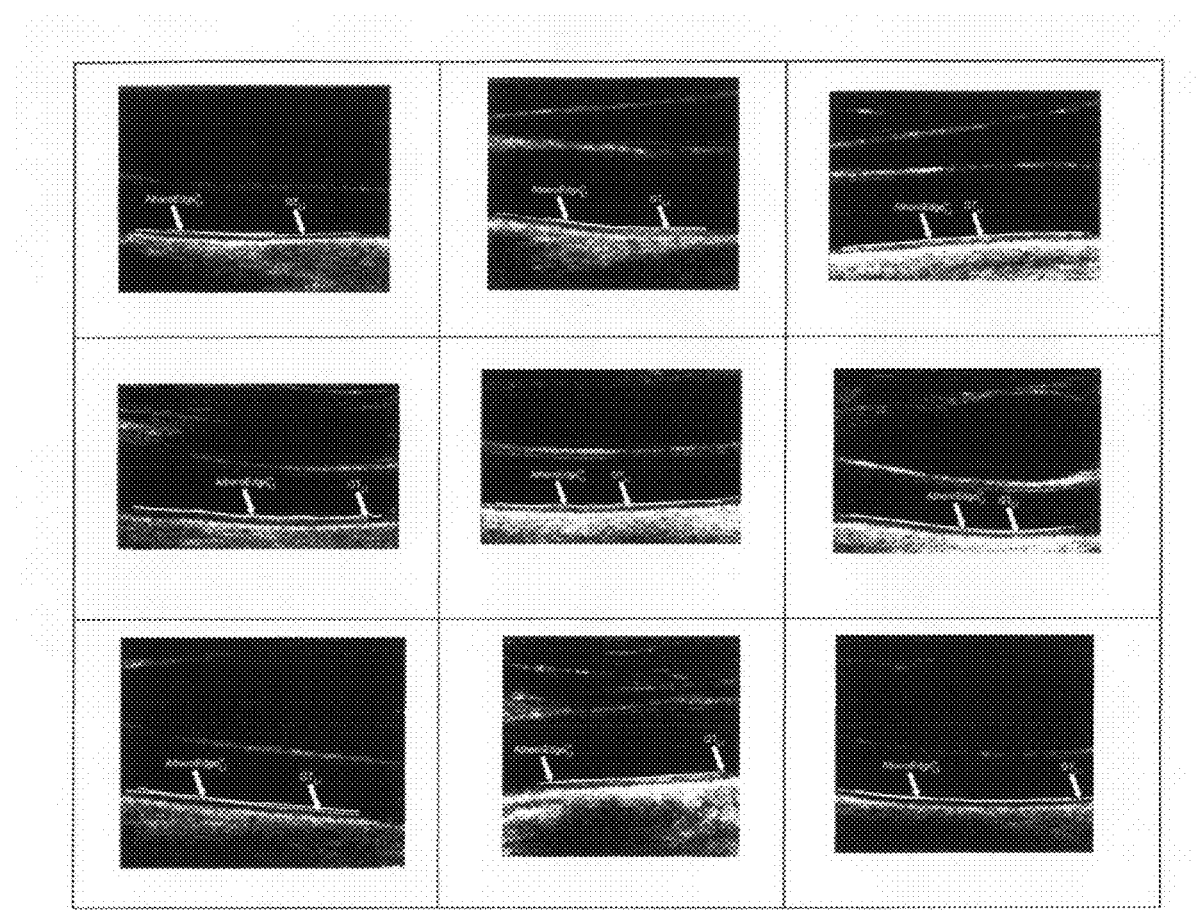
FIGURE 21 (LI Borders with respect to GT Borders)

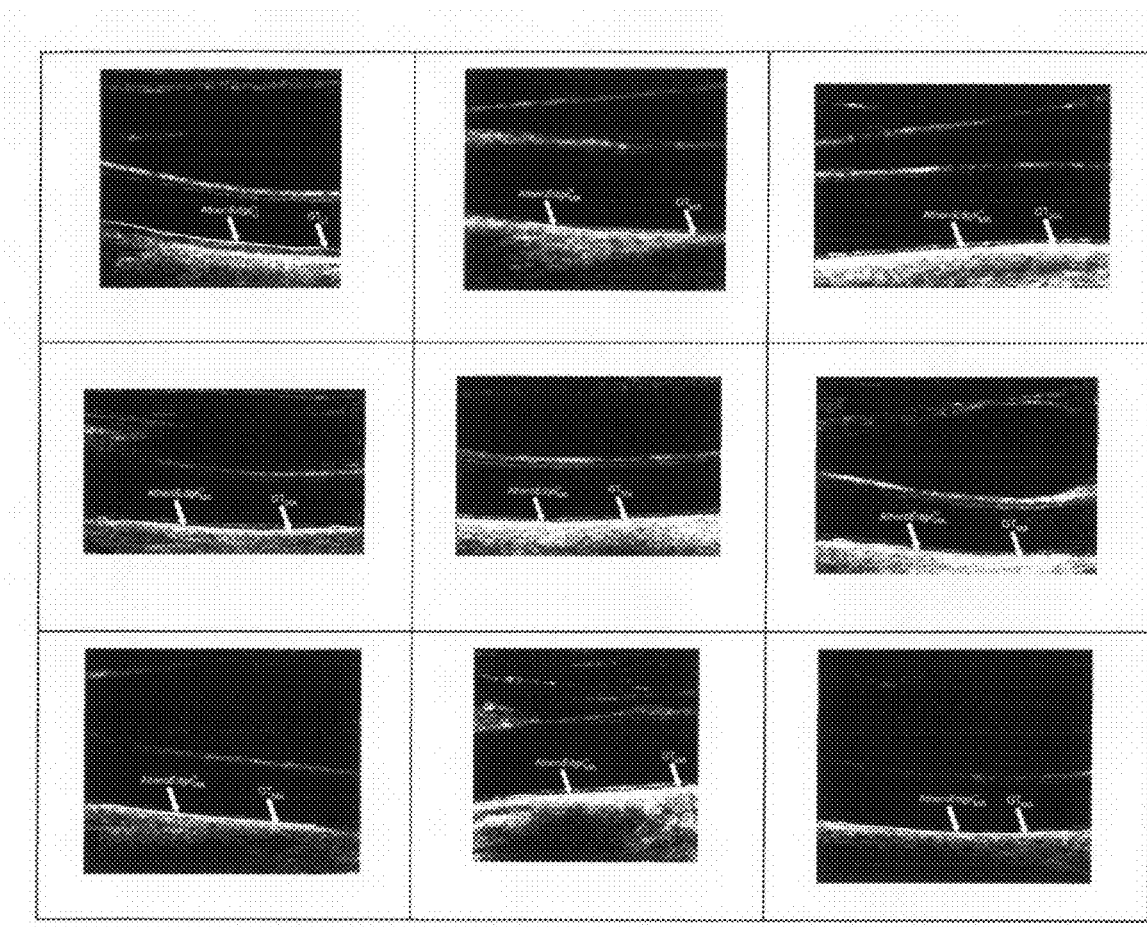
FIGURE 22 (MA Borders with respect to GT Borders)

TABLE 1 (IMT values)
| | AtheroEdge |
|---|---|
| LI Error | 1.03 ± 0.85 px |
| | 0.063 ± 0.052 mm |
| MA Error | 1.15 ± 0.83 px |
| | 0.070 ± 0.050 mm |
| IMT Error | 1.53 ± 1.89 px |
| | 0.093 ± 0.116 mm |
| IMT value | 13.36 ± 7.07 px |
| | 0.82 ± 0.44 mm |
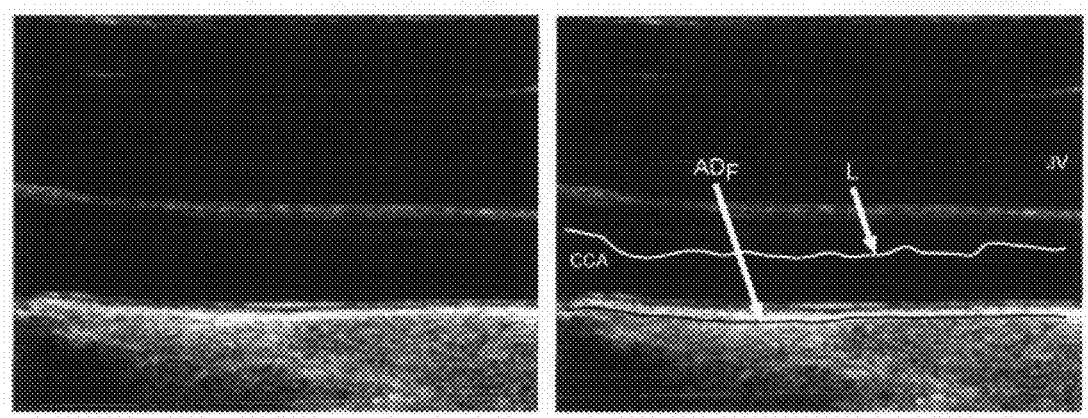
Figure 23: Stage I (using automated Artery Recognition Processor). Figure shows the Far Adventitia using local statistics (CALS)

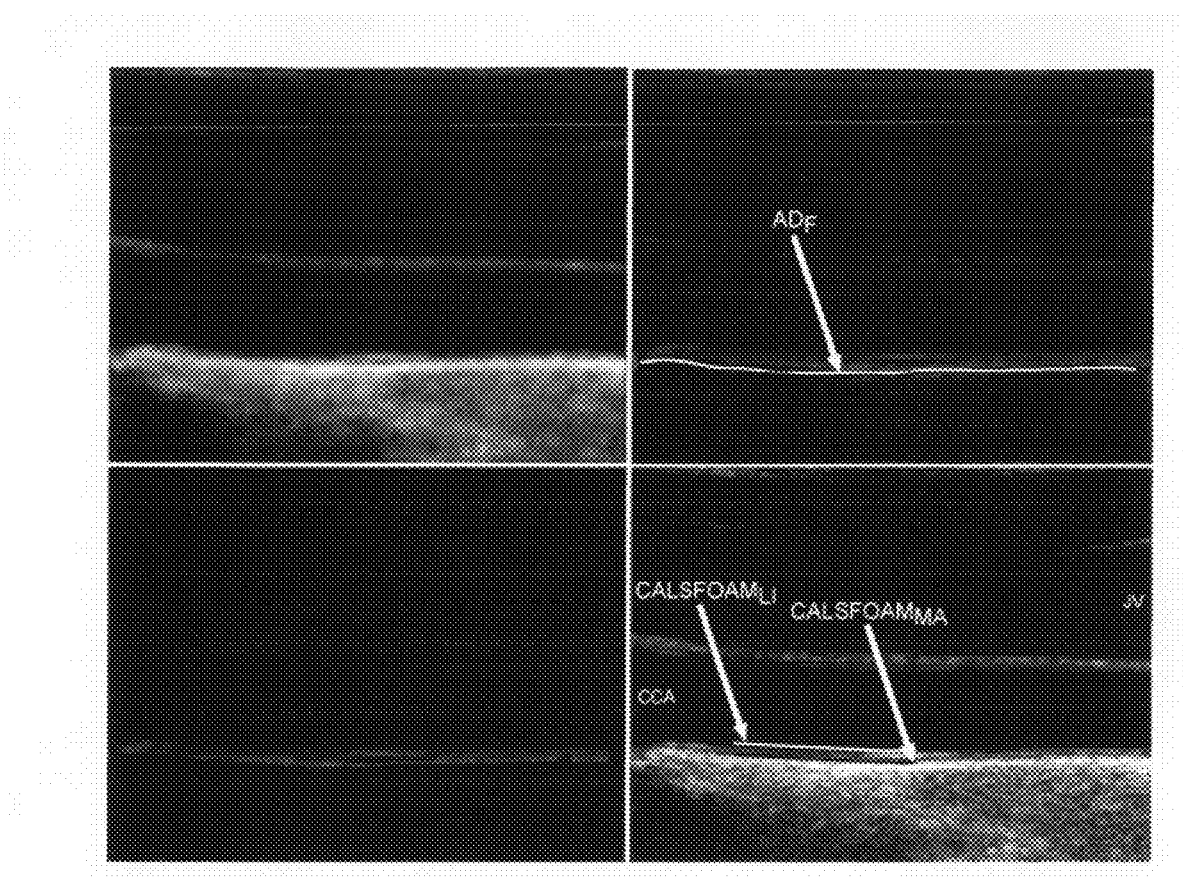
Figure 24: A) despeckled image. B) MRAFOAM operator with far adventitia overlaid. C) ROI D) CALSFOAM segmentation

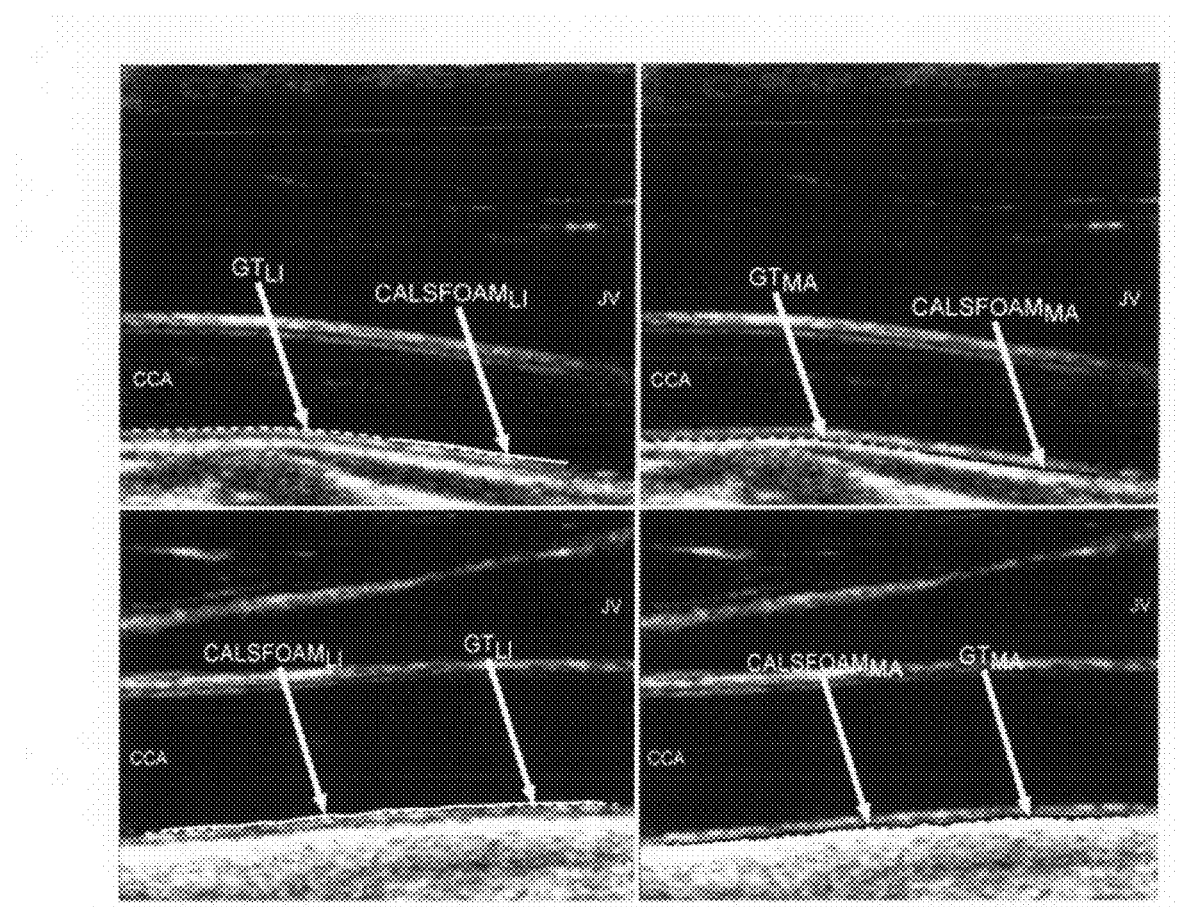
Figure 25: Figure showing the stage II output and comparing with the GT boundaries (two patients- top row and bottom row).

```
Automated Intima-Media Thickness (IMT) Measurement
         Processing Logic
              -2600-
                │
                ▼
Receive biomedical imaging data and patient demographic
    data corresponding to a current scan of a patient.
                      -2610-
                │
                ▼
    Check the biomedical imaging data in real-time to
determine if an artery of the patient has a calcium deposit
          in a proximal wall of the artery.
                     -2612-
                │
                ▼
    Acquire arterial data of the patient as a combination of
       longitudinal B-mode and transverse B-mode data.
                          -2614-
                │
                ▼
 Use a data processor to automatically recognize the artery.
                         -2616-
                │
                ▼
    Use the data processor to calibrate a region of interest
          around the automatically recognized artery.
                          -2618-
                │
                ▼
Determine the intima-media thickness (IMT) of an arterial
      wall of the automatically recognized artery.
                        -2620-
                │
                ▼
              ( End )
```

Figure 26

VASCULAR ULTRASOUND INTIMA-MEDIA THICKNESS (IMT) MEASUREMENT SYSTEM

COPYRIGHT

A portion of the disclosure of this patent document contains material that is subject to copyright protection. The copyright owner has no objection to the facsimile reproduction of the patent document or the patent disclosure, as it appears in the Patent and Trademark Office patent files or records, but otherwise reserves all copyright rights whatsoever. The following notice applies to the software and data as described below and in the drawings that form a part of this document: Copyright 2009-2010 Jasjit S. Suri, Filippo Molinari, and Biomedical Technologies Inc., All Rights Reserved.

TECHNICAL FIELD

This patent application relates to methods and systems for use with data processing, data storage, and imaging systems, according to one embodiment, and more specifically, for ultrasound image processing.

BACKGROUND

The state of Atherosclerosis in carotids or other blood vessels can be studied using magnetic resonance imaging (MRI) or Ultrasound imaging. Because ultrasound offers several advantages like real time scanning of blood vessels, compact in size, low cost, easy to transport (portability), easy availability and visualization of the arteries are possible, Atherosclerosis quantification is taking a new dimension using ultrasound. Because one can achieve compound and harmonic imaging, which generates high quality images with ultrasound, it is thus possible to do two-dimensional (2D) and three-dimensional (3D) imaging of blood vessel ultrasound images for monitoring of Atherosclerosis.

In recent years, the possibility has arisen of adopting a composite thickness of the tunica intima and media, an intima-media thickness (hereinafter referred to as an "IMT" or "CIMT") of carotid arteries, as surrogate marker for cardiovascular risk and stroke. Conventional methods of imaging a carotid artery using an ultrasound system, and measuring the IMT using an ultrasonic image for the purpose of diagnosis are being developed.

A conventional measuring apparatus can measure an intima-media thickness of a blood vessel using an ultrasound device to scan the blood vessel. Then, for example, an image of a section of the blood vessel including sections of the intima, media and adventitia is obtained. The ultrasound device further produces digital image data representing this image, and outputs the digital image data to a data analyzing device.

The intima, media and adventitia can be discriminated on the basis of changes in density of tissue thereof. A change in density of tissue of the blood vessel appears as a change of luminance values in the digital image data. The data analyzing device detects and calculates the intima-media thickness on the basis of the changes of luminance values in the digital image data. The digital image data can include a plurality of luminance values each corresponding to respective one of a plurality of pixels of the image. The data analyzing device can set a base position between a center of the blood vessel and a position in a vicinity of an inner intimal wall of the blood vessel on the image, on the basis of a moving average of the luminance values. The data analyzing device can detect a maximum value and a minimum value from among the luminance values respectively corresponding to a predetermined number of the pixels arranged from the base position toward a position of an outer adventitial wall on the image. The data analyzing device can then calculate the intima-media thickness on the basis of the maximum value and the minimum value.

The major challenges which can be affected in finding the IMT are: (a) how well the ultrasound probe is gripped with the neck of a patient to scan the carotids; (b) how well the ultrasound gel is being applied; (c) the orientation of the probe; (d) demographics of the patient; (e) presence of calcium in the proximal walls; (f) skills of the sonographer or vascular surgeon; and (g) the threshold chosen for finding the peaks corresponding to the lumen-intima (LI) border points, and the media-adventitia (MA) border points (collectively denoted herein as the LIMA or LIMA points) for each signal orthogonal to the lumen. These challenges have complicated IMT measurement using conventional systems.

Thus, a computer-implemented system and method for fast, reliable and automated processing for intima-media thickness (IMT) measurements is needed.

BRIEF DESCRIPTION OF THE DRAWINGS

The various embodiments are illustrated by way of example, and not by way of limitation, in the figures of the accompanying drawings in which:

FIG. 1 shows the calcification seen in the proximal wall (near wall) of the ICA and its corresponding shadow.

FIG. 3 show that if there is a calcium cone shadow, an embodiment computes the IMT by correcting the IMT using shadow correction. A shadow-corrected AtheroEdge process estimates the IMT values under calcium shadow projection, while AtheroEdge process runs as described herein without shadow correction, if there is no calcium shadow cone.

FIG. 5 shows how the calcium zone is estimated in the proximal (far) wall, then, how the probe orientation is changed to collect the transverse slices in the calcium zone. Finally, FIG. 5 shows how the LIMA points are determined in the transverse slices.

FIG. 11 shows that if there are "p" compartments, then the noise variance is computed by summing the variance to mean ratio of each of the "p" compartments.

FIG. 13 also shows the edge detection of the MA border by convolution of higher order derivatives of the Gaussian kernel with known mean and standard deviation. FIG. 13 also shows the up-sampling of the MA recognized border for visualization onto the high resolution cropped image.

FIGS. 16A-16C show sample images from a database of one embodiment.

FIG. 17 shows sample images of the artery recognition phase of Adventitia.

FIG. 18A shows sample images of the de-speckled filter.

FIG. 19 shows sample images of the output of the calibration stage of the system of an example embodiment.

FIG. 20 shows the LIMA border segmentation of an example embodiment.

FIG. 21 shows the LI borders with respect to Ground Truth (GT) borders.

FIG. 22 shows the MA borders with respect to Ground Truth (GT) borders.

FIG. 23 shows another embodiment of Stage I processing (using automated Artery Recognition Processor). The Figure shows the Far Adventitia using Completely Automated Local Statistics (CALS).

FIG. 24 shows: A) a despeckled image; B) a MRAFOAM operator with far adventitia overlaid; C) the region of interest (ROI); and D) CALSFOAM segmentation.

FIG. 25 shows the Stage II (calibration) output and compared with the GT boundaries (two patients—top row and bottom row).

FIG. 26 is a processing flow diagram illustrating an example embodiment of a computer-implemented system and method for fast, reliable and automated processing for intima-media thickness (IMT) measurements as described herein.

DETAILED DESCRIPTION

Figure 1:
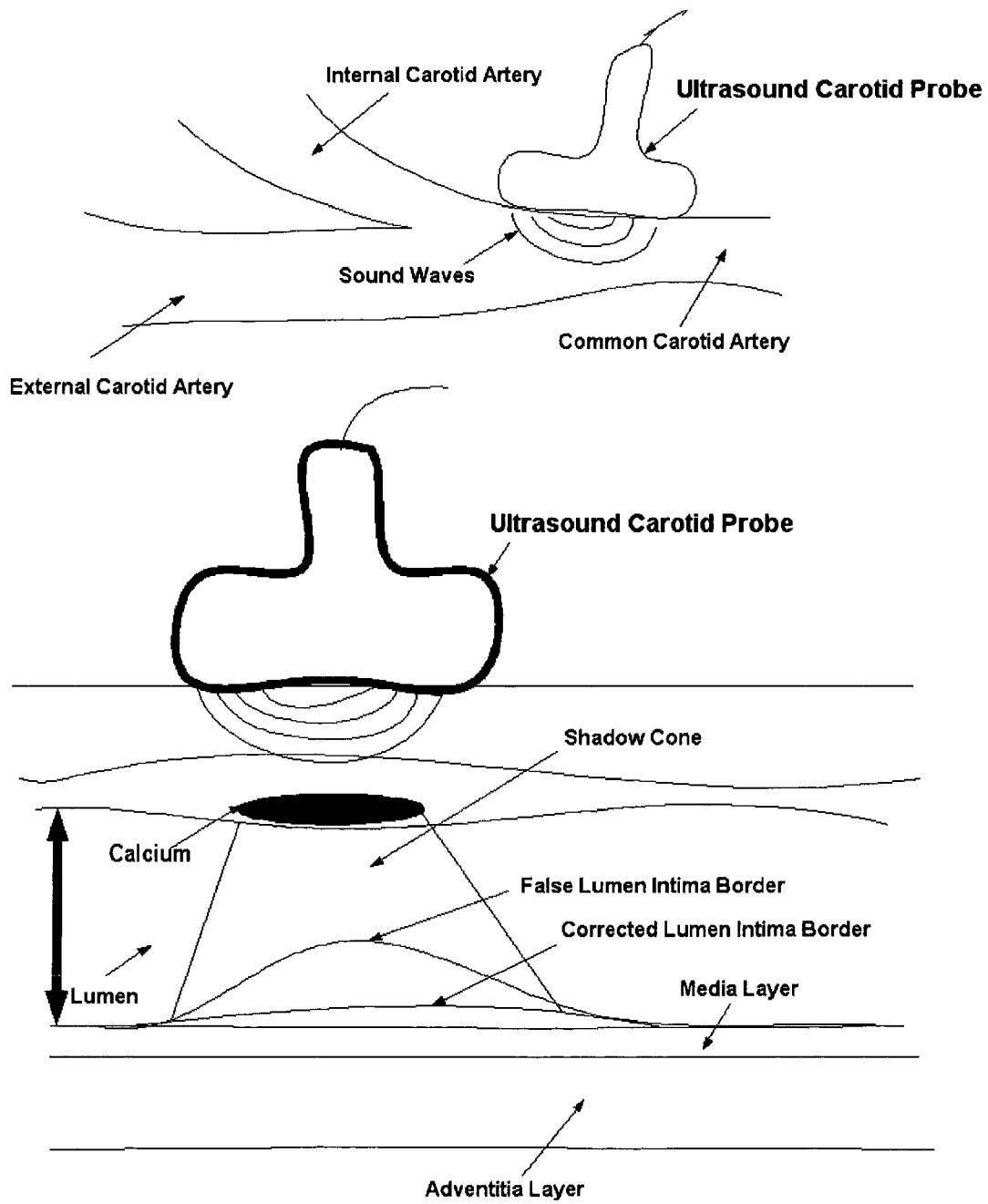
FIG. 1 shows an example of ultrasound scanning of the Carotid Artery. This can be a common carotid artery (CCA) or an internal carotid artery (ICA).

In the following description, for purposes of explanation, numerous specific details are set forth in order to provide a thorough understanding of the various embodiments. It will be evident, however, to one of ordinary skill in the art that the various embodiments may be practiced without these specific details.

This patent application discloses various embodiments of a computer-implemented system and method for fast, reliable and automated processing for intima-media thickness (IMT) measurements. In particular, this patent application discloses various embodiments of a computer-implemented system and method for intima-media thickness (IMT) measurements in the presence or absence of calcium at the near (proximal) wall of the arterial vessel. Although the embodiments disclosed herein are described in regard to particular blood vessels (e.g., carotid), the systems and methods disclosed and claimed are also applicable to IMT measurement in any blood vessel in any living organs or tissue. For example, various embodiments can be used for IMT measurement in carotid, femoral, brachial and aortic arteries. The details of various example embodiments are provided herein.

Overview of Various Embodiments

In the various example embodiments described herein, a variety of benefits and advantages are realized by the disclosed systems and methods. A representative sample of these advantages is listed below.

(A) Coarse to Fine Resolution Processing: Previous art has focused on methods for either classification of media layer or finding the MA edges in the manual designated region of interest (ROI). Because conventional systems may use a manual method in a ROI, it is time consuming and non-practical for clinical trials and where the need is to process hundred's of patients a day or where there is very little time for examination or where the image quality may not be very good in terms of signal-to-noise ratio (SNR) or CNR or where the proximal wall may have a lot of calcium. In contrast, in the various embodiments described herein, we have developed a new method which is fast, accurate, reliable and very practical for IMT measurement for carotids, brachial, femoral and aortic blood vessels. Because the manual methods are time consuming and require a lot of training, the automated methods described offer strong advantages over current schemes. In an example embodiment described herein, a two stage automated process is described: (a) automated artery recognition, and (b) automated calibration, which finds the LIMA borders more accurately. The automated recognition process is difficult, given the Jugular vein in the neighborhood. Our system recognizes the artery in a smaller image with a high speed (denoted herein as a coarse resolution) scan and isolates the artery. The isolated artery can then be seen in a fine resolution or high resolution scan. This allows processing the pixels in the correct region of interest. In this manner, a multi-resolution process is used. The statistics of the neighboring pixels will not affect the region of interest, which is where the accurate LIMA borders need to be determined. Normally, arteries are about 10-15 mm wide while the media thickness is about 1 mm wide. It is also known from our experience that the image resolution is about 15 pixels per mm. If we can bring the original resolution to a coarse resolution by performing a one step down sample, we can bring the media layer to about 8 pixels per mm. Further, if this coarse resolution is down sampled by another half, then one can bring the image resolution from 8 pixels/mm to 4 pixels/mm. Thus, if the coarse resolution of the arterial ultrasound vessels has a medial thickness of 4 pixels/mm, one can easily detect such edges by convolving the higher order derivatives of Gaussian kernel with the coarse resolution image. Thus, a novel feature of a particular embodiment is to automatically detect the arterial wall edges by down sampling the image and convolving the coarse images to higher order derivatives of Gaussian kernels. This allows the media layer to be automatically determined. Such an approach for automated media layer detection from fine to coarse resolution will further improve the region of interest determination. The art of changing the fine to coarse resolution in a general sense has been popular in computer vision sciences. There are several general methods available to converting the image from high resolution to coarse resolution. One of these general methods is a wavelet-based method where wavelets are applied for down sampling the image to half. Another method can be a hierarchical down sampling method using a pyramid approach. Thus, one advantage of the current system is automated recognition of the artery at coarse resolution and then using the Far Adventitia border for visualization and recognition at the fine resolution (up-sampled resolution). This approach, as described herein, has several advantages:

(1) Robustness and Accurate Wall Capture: The approach, as described herein, is very robust, because the higher order derivative kernels are very good in capturing the vessel walls (e.g., see, A Review on MR Vascular Image Processing Algorithms: Acquisition and Pre-filtering: Part I, Suri et al., IEEE TRANSACTIONS ON INFORMATION TECHNOLOGY IN BIOMEDICINE, VOL. 6, NO. 4, pp. 324-337, DECEMBER 2002; and A Review on MR Vascular Image Processing:Skeleton Versus Nonskeleton Approaches: Part II, Suri et al., IEEE TRANSACTIONS ON INFORMATION TECHNOLOGY IN BIOMEDICINE, VOL. 6, NO. 4, DECEMBER 2002).

(2) Faster than the conventional processing: Because the recognition is strategized at coarse level and down sampled once or twice from its original size of the image, it is therefore processing ½ A or ¼$^{th}$ the number of pixels for automated recognition of the media layer. This improves the speed of the system.

(3) Independent of Orientation of the vascular scan: Another major advantage to the system is that these Gaussian kernels are independent of the orientation of the blood vessels in the image. Because the ultrasound vascular scans do not always have the vessel orientation horizontal with respect bottom edge of the image, manual methods can pose a further challenge towards the region of interest estimation.

(4) Guiding Method for the Calibration System: Because the calibration phase is followed by the recognition phase, the calibration system becomes very robust because the calibration processing is done in the region of interest determined by the automated recognition system. It is like a master and slave process. The master being the recognition phase and calibration being the slave. Thus, the calibration system adds the value determined by the automated recognition system for vascular ultrasound such as IMT measurement for carotid, femoral, aortic and brachial. Such a combination where the calibration system is guided by the automated recognition system helps in mass processing of huge database processing, real time processing, and processing where the arterial layout in the image has lot of variability.

(5) Running the Mass IMT system for Clinical Analysis: Because the recognition is automated followed by the calibration system, an important benefit such a system would deliver is its real time use for analysis of IMT measurement on large databases. Running clinical databases on still images would be even more beneficial because such a system would be completely automated in terms of recognition and IMT measurement.

(6) Applications: Because the ultrasound probes use almost the same frequency of operation for scanning the vascular arteries such as carotid, femoral, brachial and aortic, it is thus possible to use such an architectural system for these classes of blood vessels.

(B) In the prior art, we have seen that speckle reduction has been used generally for removing speckles in ultrasound images. Though, speckle reduction is common in ultrasound imaging, the way speckle reduction is used in the various embodiments described herein is very conservative. The idea here is to find out where the Far Adventitia borders are using an automated recognition system and then apply the local statistical speckle reduction filter in a specific set of pixels, which come under the LIMA band or media layer. Such a strategy provides multiple advantages:

(1) Avoiding Large Computation Times on Speckle Reduction: The computation time for speckle reduction is not wasted in such a paradigm, unlike conventional methods, where the speckle reduction is part of the whole streamline flow and is being run on the whole image.

(2) Speckle Reduction is implemented on the original raw intensity in the region estimated at a Coarse Resolution: In an example embodiment, the speckle reduction filter is run in the automatically recognized region (e.g., the MA borders), which is actually applied on the original image rather than on the coarse image. This way, the original speckles are removed thereby preserving the intensities of high gradient structures like LI and MA peaks. This is very important because the calibration system acts on these speckle reduced regions of interest.

(3) Guidance to the Calibration System: The calibration system is guided by the speckle reduction filter, which is optimized for the region of interest.

(C) Extracting LIMA borders in the presence of Calcium Shadow: Calcium is an important component of the media layer. It is not exactly known how the calcium is formed in a blood vessel, but it is said that calcium accumulates in the plaques. During the beginning of Atherosclerosis disease, the arterial wall creates a chemical signal that causes a certain type of WBC (white blood cells) such as monocytes and T cells that attach to the arterial wall. These cells then move into the wall of the artery. These T cells or monocytes are then transformed into foam cells, which collect cholesterol and other fatty materials and trigger the growth of the muscle cells (which are smooth in nature) in the artery. Over time, it is these fat-laden foam cells that accumulate into plaque covered with a fibrous cap. Over time, the calcium accumulates in the plaque. Often times, the calcium is seen in the near wall (proximal wall) of the carotid artery or aortic arteries. The presence of a calcium deposit on a blood vessel wall can cause an acoustic shadow region in an ultrasound image and a resulting shadow cone formation in the distal wall (far wall). As a result, the LI boundaries can be over computed from its actual layer. The shadow causes the LI lining to be mis-interpreted over the actual LI boundary. As a result, the LI-MA distances (IMT values) are over computed in the shadow zone. Because of this, the IMT formation is over computed in these cases. FIG. 1 shows an example of ultrasound scanning of the Carotid Artery. FIG. 1 also shows the calcification seen in the proximal wall (near wall) of the ICA and its corresponding shadow.

The various embodiments described herein accurately process the IMT computation even in the presence of a shadow cone formation. As described in more detail herein, the actual LI boundaries are recovered if calcium is present causing the shadow cone. As a result, the IMT computation of the various embodiments has the following advantages when shadow cones are encountered.

(1) Accurate IMT computation in real time when the calcium is present in the proximal wall (near wall) causing the shadow cone formation; and (2) The system allows computing the IMT in both cases: (a) when calcium is present and when calcium is not present.

BRIEF SUMMARY OF EXAMPLE EMBODIMENTS

In the various example embodiments described herein, a computer-implemented system and method for fast, reliable and automated processing for intima-media thickness (IMT) measurements is disclosed. The completely automated technique described herein can be denoted as AtheroEdge, the AtheroEdge system, or the AtheroEdge process. The AtheroEdge process of an example embodiment includes two steps: (i) the automated recognition of the carotid artery (CA) in the image frame, and (ii) the segmentation of the far CA wall. The automatically traced LI and MA profiles are used to measure the IMT.

Cropping System: Preliminarily, the raw ultrasound image is automatically cropped in order to discard the surrounding black frame containing device headers and image/patient data. If the image came in DICOM format (Digital Imaging and Communications in Medicine format), data can be used as contained in the specific field named SequenceOfUltrasoundRegions, which contains four sub-fields that mark the location of the image containing the ultrasound representation. These fields are named RegionLocation (their specific label is $x_{min}$, $x_{max}$, $y_{min}$ and $y_{max}$) and they mark the horizontal and vertical extension of the image. The raw B-Mode image is then cropped in order to extract only the portion that contains the carotid tissue morphology. Those of ordinary skill in the art of DICOM will know that if the image came in from other formats or if the DICOM tags were not fully formatted, one can adopt a gradient-based procedure. For non-DICOM images, we computed the horizontal and vertical Sobel gradient of the image. The gradients repeat similar features for the entire rows/columns without the ultrasound data: they are zero at the beginning and at the end. Hence, the beginning of the image region containing the ultrasound data can be calculated as the first row/column with gradient different from zero. Similarly, the end of the ultrasound region is computed as the last non-zero row/column of the gradient. FIG. 16A shows the original DICOM images in few samples (10 different images), while FIG. 16B shows the automated cropped images.

Automatic Recognition of the CA: To automatically identify the CA in the image frame, we developed a novel and low-complexity system and procedure. The following sample steps are used for automatic CA recognition, starting with the automatically cropped image which constitutes the input of the procedure.

Downsampling. The image is first down-sampled by a factor of two (i.e., the number of rows and columns of the image was halved).

Speckle reduction. Speckle noise is attenuated by using a conventional first-order statistics filter, which gives satisfactory performance in the specific case of carotid imaging. This filter is defined by the following equation:

$$J_{x,y} = \bar{I} + k_{x,y}(I_{x,y} - \bar{I}) \quad (1)$$

where, $I_{x,y}$ is the intensity of the noisy pixel, $\bar{I}$ is the mean intensity of a N×M pixel neighborhood and $k_{x,y}$, is a local statistic measure. The noise-free pixel is indicated by $J_{x,y}$. As conventionally known, $k_{x,y}$ can be mathematically defined, $$k_{x,y} = \frac{\sigma_I^2}{\bar{I}^2 \sigma_I^2 + \sigma_n^2},$$

where $\sigma_I^2$ a represents the variance of the pixels in the neighborhood, and $\sigma_n^2$ the variance of the noise in the cropped image. An optimal neighborhood size in a particular embodiment was shown to be 7×7 pixels.

Higher order Gaussian derivative filter. The despeckled image is filtered by using a first order derivative of a Gaussian kernel filter. It is possible to observe how the CA walls become enhanced to white. The sigma parameter of the Gaussian derivative kernel is taken equal to 8 pixels, i.e. to the expected dimension of the IMT value. In fact, an average IMT value of, say 1 mm, corresponds to about 16 pixels in the original image scale and, consequently, to 8 pixels in the down-sampled scale.

Far adventitia automated tracing. To automatically trace the profile of the far wall, the process of an example embodiment uses a heuristic search applied to the intensity profile of each column. Starting from the bottom of the image (i.e. from the pixel with the higher row index), the process of an example embodiment searches for the first white region of at least 6 pixels of width. The deepest point of this region (i.e. the pixel with the higher row index) marks the position of the far adventitia ($AD_F$) layer on that column. The sequence of all the points of the columns constitutes the overall $AD_F$ automatically generated tracing.

Up-sampling. The $AD_F$ profile is up-sampled to the original scale and overlaid to the original image. At this stage, the CA far wall is automatically located in the image frame and automated segmentation is made possible.

Calibration Phase: The process of an example embodiment can build a region-of-interest (ROI) around the automatically traced $AD_F$ profile. The ROI has the same width of the $AD_F$ curve. The height is equal to 30 pixels (1.8 mm for images with 16.67 pixels/mm of density, and 1.875 mm for images with 16 pixels/mm of density): for each point of the $AD_F$ profile, a particular embodiment can consider as upper limit of the ROI the pixel with a row index of 30 pixels lower. Substantially, the bottom limit of the ROI is the $AD_F$ curve and the upper limit the $AD_F$ but shifted upwards of 30 pixels.

The process of an example embodiment can use a calibration operator as a segmentation strategy. The calibration operator is an edge detector with good accuracy and robustness to noise. Such calibration operators are known in the art. One such example follows:

$$e(x,y) = \frac{1}{A_\theta} \int \int_\theta |I_1(x,y) - I_2(x-x', y-y')| \cdot G(x, y, \sigma_r) \, dx' dy' \quad (2)$$

where $I_1(x,y) = I(x,y) \otimes G(x,y,\sigma_1)$ and $I_2(x,y) = I(x,y) \otimes G(x,y,\sigma_2)$ are computed by low-pass filtering the input image $I(x,y)$ by a Gaussian kernel with standard deviations equal to $\sigma_1$ and $\sigma_2$, respectively in the region of interest. This low-pass filtering step is required in order to cope with images having low values of signal-to-noise. The third Gaussian kernel $G(x,y,\sigma_r)$ is a regularization and weighting term. When computed in a homogeneous region, the calibration edge operator $e(x,y)$ is zero valued. When computed in presence of a gray level discontinuity, the value of $e(x,y)$ increases. In a particular embodiment, we use $\sigma_1 = \sigma_r = 0.3$ mm and $\sigma_2$ equal to 0.6 mm. Such values were tuned according to the image's resolution.

The LI and MA interfaces can then be searched by relying on heuristic search. The LI and MA transitions originate two high-intensity peaks on the calibration profile, which can be automatically marked. For each intensity profile (i.e. for each column of the ROI), the system marks the position of the higher intensity local maximum. Let $MRAMAX_1$ be the intensity of this local maximum. Then, the system searches for a second local intensity maximum with a height $MRAMAX_2 \geq 0.1\, MRAMAX_1$. The system marks the position of this second local maximum. Then, the system searches for a local minimum comprised between $MRAMAX_1$ and $MRAMAX_2$. If such minimum is found, the system assigns $MRAMAX_1$ and $MRAMAX_2$ to the LI and MA interfaces. The deepest maximum is assigned to MA, the uppermost to LI. The sequence of all the LI and MA points of each column produces the final segmentation of the far carotid wall.

DETAILED DESCRIPTION OF EXAMPLE EMBODIMENTS

This patent application discloses various embodiments of a computer-implemented system and method for fast, reliable and automated processing for intima-media thickness (IMT) measurements. In particular, this patent application discloses various embodiments of a computer-implemented system and method for intima-media thickness (IMT) measurements in the presence or absence of calcium at the near (proximal) wall of the arterial vessel. Although the embodiments disclosed herein are described in regard to particular blood vessels (e.g., carotid), the systems and methods disclosed and claimed are also applicable to IMT measurement in any blood vessel in any living organs or tissue. For example, various embodiments can be used for IMT measurement in carotid, femoral, brachial and aortic arteries. The details of various example embodiments are provided herein.

IMT measurement is a very important risk marker of the Atherosclerosis disease. Typically, there are two ways to measure the arterial IMT's: (a) invasive methods and (b) non-invasive methods. In invasive methods, traditionally, intravascular ultrasound (IVUS) is used for measuring vessel wall thickness and plaque deposits where special catheters are inserted in the arteries to image them. Conventional ultrasound is used for measuring IMT non-invasively, such as from carotid, brachial, femoral and aortic arteries. The main advantages of non-invasive methods are: (i) low cost; (ii) convenience and comfort of the patient being examined; (iii) lack of need for any intravenous (IV) insertions or other body invasive methods (usually), and (iv) lack of any X-ray radiation; Ultrasound can be used repeatedly, over years, without compromising the patient's short or long term health status. Though conventional methods are generally suitable, conventional methods have certain problems related to accuracy, speed, and reliability.

The IMTs are normally 1 mm in thickness, which nearly corresponds to 15 pixels on a typical screen or display. IMT estimation having a value close to 1 mm is a very challenging task in ultrasound images due to large numbers of variabilities such as: poor contrast, orientation of the vessels, varying thickness, sudden fading of the contrast due to change in tissue density, presence of various plaque components in the intima wall such as fibrous muscles, lipids, calcium, hemorrhage, etc. Under normal resolutions, a 1 mm thick media thickness is difficult to estimate using stand-alone image processing techniques. Over and above, the image processing algorithms face an even tighter challenge due to the presence of speckle distribution. The speckle distribution is different in nature from these interfaces. This is because of the structural information change between intima, media and adventitia layers of the vessel wall. As a result, the sound reflection from different cellular structures is different. The variability in tissue structure—all that happens in 1 mm of the vessel wall—brings fuzziness in the intensity distribution of the vessel wall. Under histology, media and adventitia walls are clearly visible and one can observe even their thicknesses. This 1 mm zone is hard to discern in a normal resolution image of 256×256 pixels in a region of interest (ROI) or in a higher resolution image of 512×512 pixels in a region of interest (ROI). One needs a high resolution image to process and identify the intensity gradient change in ultrasound images from lumen to intima and media to adventitia layers. The ultrasound image resolution may not be strong enough like magnetic resonance imaging (MRI) or computerized axial tomography (CAT or CT) images, which can be meaningful for soft tissue structural information display.

There are two ways to process and identify the intensity gradient change in ultrasound images from lumen to intima (LI) and media to adventitia (MA) layers: (a) have a vascular surgeon draw the LI/MA borders and compute the IMT image interactively, OR (b) have a computer determine the LI and MA borders along with IMT's. Case (a) is very subjective and introduces variability in the IMT estimation. IMT screenings are really part of the regular check-up for patients and millions of scans are done each day around the world. The manual handling of such a repetitive work flow of IMT screenings is tedious and error-prone. Case (b) is difficult to implement, because it is difficult to identify the LI and MA borders with heavy speckle distribution and the inability of ultrasound physics to generate a clear image where the semi-automated or automated image processing methods are used for IMT estimation. Besides that, the calcium deposit in the near walls causes the shadow.

Figure 3:
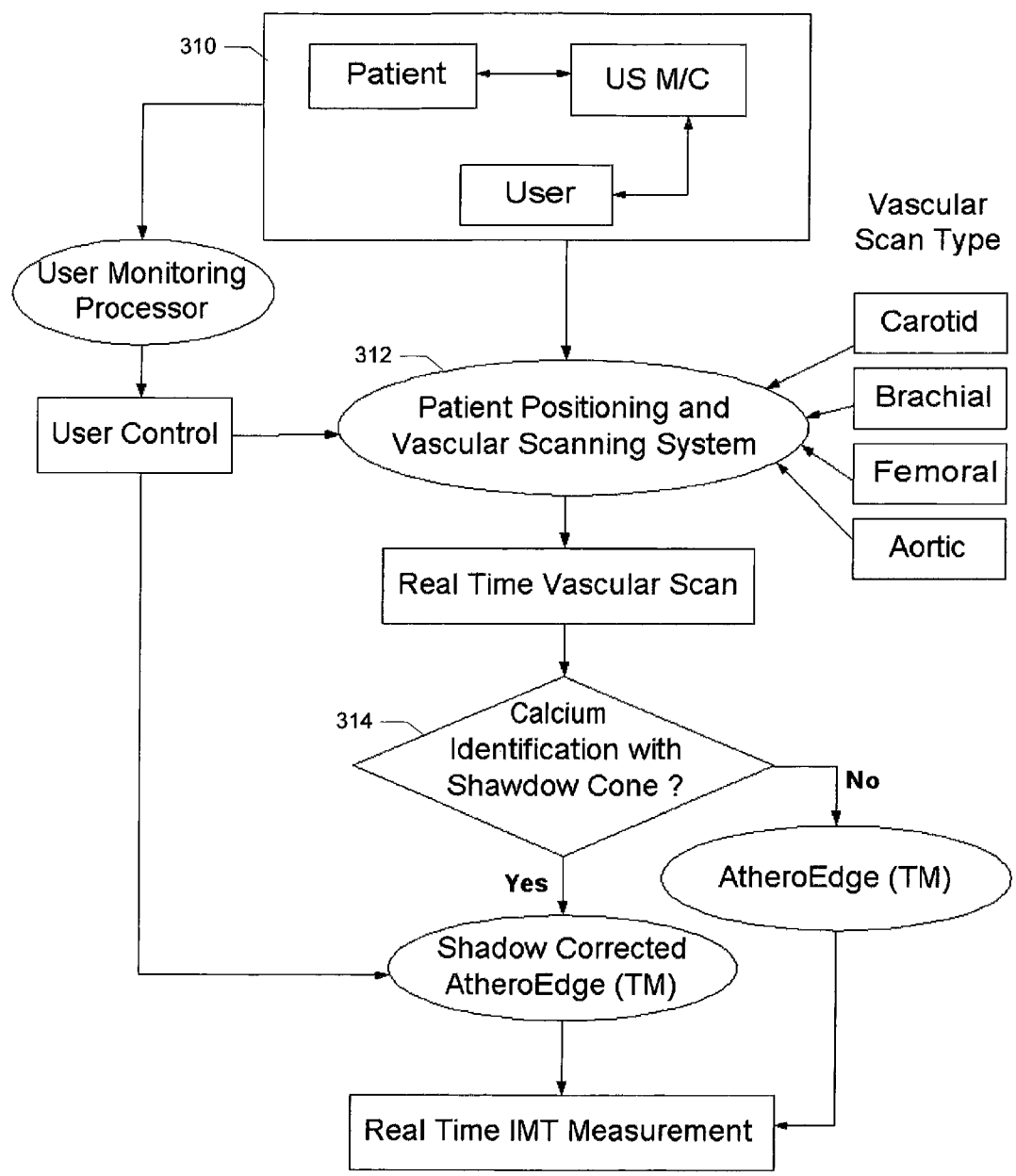
FIG. 3 shows the overall system of an example embodiment, which can be applied for computation of the IMT for any kind of vascular ultrasound data such as coming from Carotid, Brachial, Femoral and Aortic. A particular embodiment is denoted herein as the AtheroEdge process.

FIG. 3 shows the OPD (object process diagram) for the whole system of an example embodiment. The top box 310 shows the interacting system between the ultrasound machine, patient, and the user. Various embodiments are applicable to vascular ultrasound for carotid, brachial, aortic and femoral, but not limited to these alone. For carotid, one can use the left and the right scan. When the patient presents, the system is prepared for the ultrasound scan and IMT measurement. Patient is positioned optimally for the best scan and then ultrasound gel is applied before vascular scanning. The probe is then skin surfaced for the carotid scan as seen in the FIG. 1. The first sub-system 312 in FIG. 3 shows the patient positioning and vascular scanning system. The input to this block is vascular scan type: carotid, brachial, femoral and aortic, which means these four kinds of arteries can be used for IMT measurement in a particular embodiment. The output to the system can be the real time ultrasound vascular scan, normally DICOM in format. FIG. 3 also shows that the user completely monitors the system all the time and the system is in the user's control all the time. This allows for perfect synchronization of the patient interface with ultrasound and for the diagnostic IMT measurement system. Normally, the vascular screening is done by the vascular surgeon or a neuroradiologist or a sonographer or a cardiologist. They are trained to recognize any calcium present near the proximal (near) wall zone. The diamond box 314 shows if the calcium is present in arterial wall or not. The user, such as a neuroradiologist or sonographer or cardiologist or vascular surgeon uses his/her expertise to spot the calcium and its shadow in the proximal (near) end of the arterial wall. Those of ordinary skill in the art will note that even though the probe is used longitudinally in B-mode for scanning the arterial wall, one can change the orientation of the probe orthogonal to the blood flow and move the probe linearly along the carotids or brachial or femoral or arotic to get the transverse slices to see the extent (range) of the calcium.

Because the presence of the calcium in longitudinal B-mode scans causes the calcium shadow cone in the ultrasound images, a different processing stage is required before the AtheroEdge process and stand alone system is applied for IMT measurement. The AtheroEdge process of an example embodiment is made to activate if there is no calcium present, while the AtheroEdge system with calcium correction is made to activate when calcium is spotted in the longitudinal or transverse B-mode images. The output of the AtheroEdge process (with or without calcium correction) is the real time IMT measurement. Note that the user completely monitors the system all the time and the system is in the user's control all the time during the AtheroEdge system operation with calcium and the AtheroEdge system operation without calcium.

Figure 2:
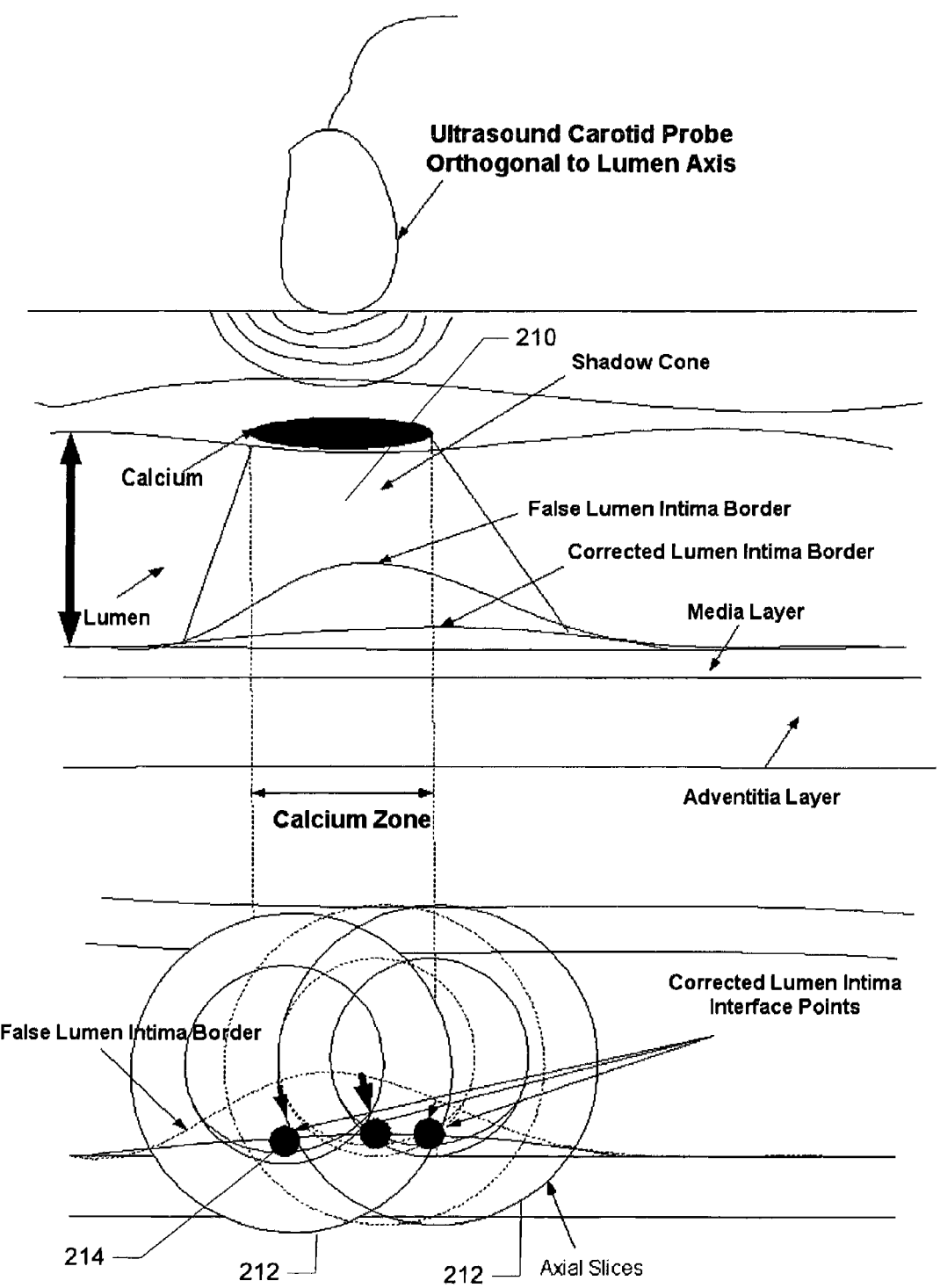
FIG. 2 shows the solution of the calcification issue, where the transverse slices are acquired instead of B-mode longitudinal images. These transverse slices are depicted as circular cross-sectional shapes in the image.

FIG. 1 shows the diagrammatic view where calcium is present in the proximal wall. As can be seen in FIG. 1, a black region can be present in the image in the intima layer or media layer or in the lumen region, but hanging from the intima layer. There are many variabilities of how the calcium can stick or hang in the proximal wall. But in every case, there will be a shadow caused when ultrasound is blocked by this calcium present in the arterial wall (see the details by Robin Steel et al., Origins of the edge shadowing artifact in medical ultrasound imaging, Ultrasound in Med. & Biol., Vol. 30, No. 9, pp. 1153-1162, 2004). It has been shown that calcification causes echogenity in the ultrasound image to be hypoechoic (darker) and covers the true reflection coming out of the media layer of the distal (far) borders. Okuda et al. showed these kinds of hypoechoic zones in the ultrasound images due to the presence of calcium in the renal arteries (see, Okuda et al., Sonographic Features of Hepatic Artery Calcification in Chronic Renal Failure, Acta Radiologica 44, 2003. 151-153). IMT measurements in such cases can become difficult or challenging. The various embodiments described herein not only find the reliable and automated IMT measurements in ordinary arterial walls, but also find the reliable and automated IMT measurements in the presence of calcification. FIG. 2 shows the calcification of the proximal end of the wall and the shadow cone made by the calcification and projected onto the distal (far) end of the wall. Due to this calcification as shown in FIGS. 1 and 2, the LI borders are over calculated or not accurately calculated. As described herein, various embodiments can correct the LI borders for the distal (far) end of the wall. This correction has to be applied in the region where calcification is present.

Thus, the various embodiments described herein provide a method, which can actually compute the IMT values if the user (cardiologist, neuroradiologist, vascular surgeon, sonographer) does not find the calcium shadows. As such, the various embodiments described herein provide a reliable, real time and accurate method for IMT measurement when there is no calcium present. Similarly, the various embodiments described herein provide a reliable, real time and accurate method for IMT measurement when there is calcium present. When calcium is not present, the IMT computation uses the AtheroEdge process as described herein directly, but when calcium is present the system uses the AtheroEdge process in the non-calcium zones and correcting the LI border in the calcium zones and then interpolating with the LI border of the non-calcium zone thereby getting the complete and correct LI borders.

FIG. 2 shows the methodology of an example embodiment used for correcting the LI borders when the calcium shadow cones 210 are present. The method uses a combination of data acquisition and software method for correcting the LI borders. These two steps are done in real time while the ultrasound probe is still proximate to the patient's artery. The combinational approach requires no change by the expert user (cardiologist, neuroradiologist, vascular surgeon, sonographer, or the like) who has been trained to use the probe on arterial anatomy. The holding method of using the probe still uses the same art by making the grip of four fingers and one thumb. The only change the user has to do is rotate his/her wrist 90 degrees to the longitudinal axis. Once the calcium region is identified, the user (cardiologist, neuroradiologist, vascular surgeon, sonographer, or the like) rotates the orientation of the probe by rotating his/her wrist and taking the scans of the distal (far) wall. Because the probe is oriented orthogonally to the longitudinal axis of the arterial vessel, the images captured are axial or transverse in nature. The user then moves the probe with a reasonable speed linearly and while moving the probe, the transverse images are captured. The user can stop the linear movement of the probe as soon as the full extent of the calcium region has been scanned.

These axial slices 212, captured with the probe oriented orthogonally to the longitudinal axis of the arterial vessel, will show the vessel wall as a circular band in nature. The inner wall shows the lumen region and outer wall is the adventitia walls. Because we are interested in the distal (far) walls in longitudinal B-mode, the system must ensure orthogonal scans for the vessel wall region in the distal area of the artery. Those of ordinary skill in the art of 3D ultrasound will notice that the lumen region is dark (black) and the vessel wall (relatively brighter than lumen region), hence the interface region is discernable between lumen and walls. This change in gradient information for the distal (far) wall for that particular slice will allow the user manually or semi-automatically or automatically to estimate the gradient change between the lumen and vessel wall for that orthogonal slice. FIG. 2 shows the circular wall boundaries of the lumen and media-adventitia layers in axial or transverse slices 212. The point of gradient change between the lumen and vessel wall corresponding to the longitudinal B-mode position of the probe, orthogonal to the arterial axis is the point, which corresponds to the LI border where the calcium region was hit. This point 214 is shown as a black circle in the FIG. 2. Those of ordinary skill in the art of boundary estimation can use an off-the-shelf snake method or deformable method or edge detection method to find the lumen boundary in the transverse slice of the ultrasound arterial image. The above process of finding the point of intersection of the longitudinal B-mode position to the circular vessel wall in the transverse image is repeated for all the transverse slices where the calcium region is identified in proximal wall. The information extracted for the shadow region is stored to be reused because that is the partial information on the LI border. The rest of the information will be extracted from the AtheroEdge process using the longitudinal B-mode vascular ultrasound image.

Figure 4:
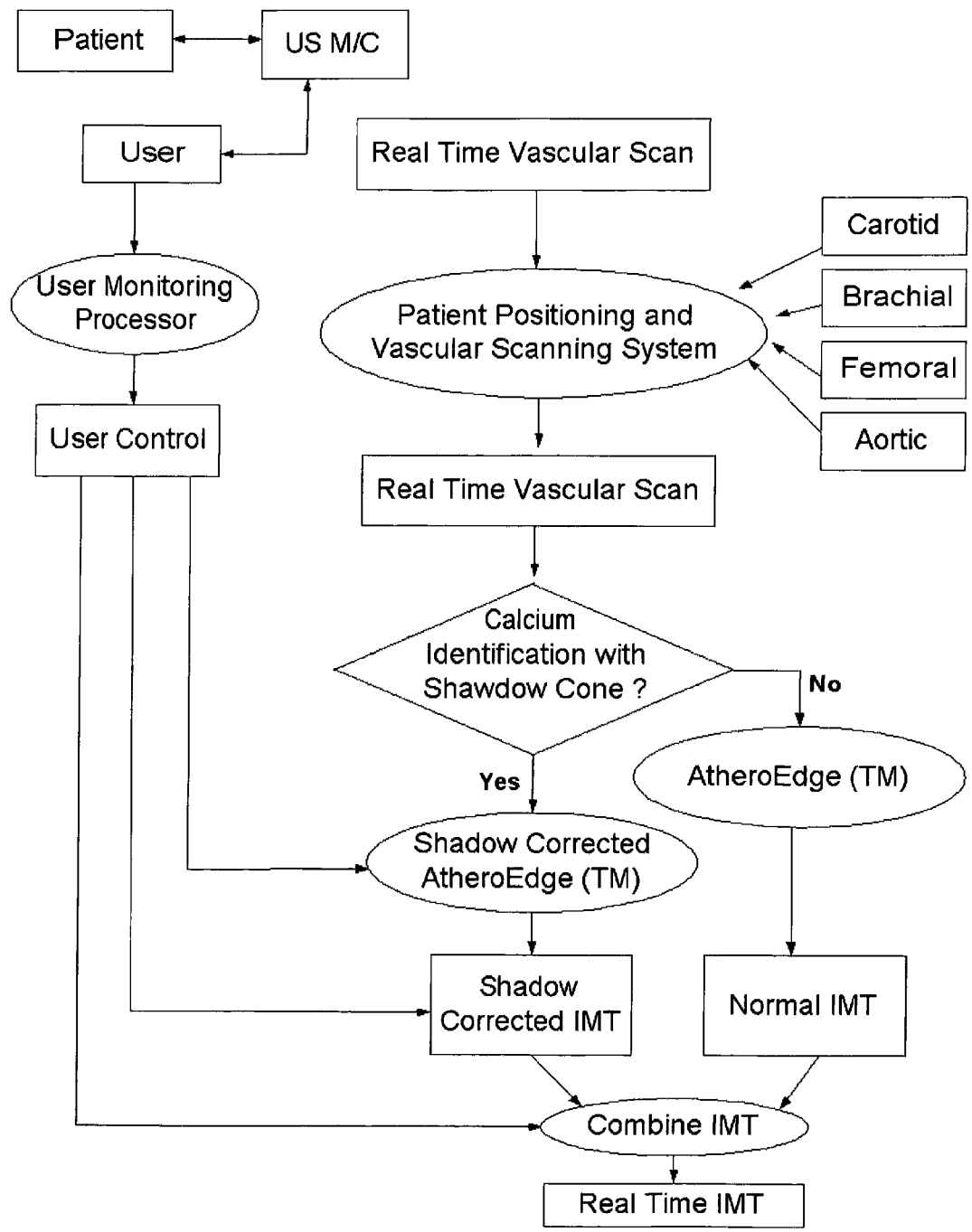
FIG. 4 shows an example of how the IMT values are combined with and without shadow cones. If there are no shadow cones (or calcium present), then the AtheroEdge process computes the real time IMT without shadow correction.

FIG. 4 actually shows the system of an example embodiment, which helps in combining the corrected LI boundary information from the calcium shadow zone (shadow corrected the AtheroEdge process) and LI boundary information for the non-calcium shadow zone. This will lead to the formation of the full LI boundary and MA boundary leading to the distance measurement called IMT. This can be seen in the example of FIG. 4. During the complete process, we must ensure that the user is in full control and has a fall back system should the automated system encounter a challenge, thereby changing to the semi-automated system. If the user (cardiologist, neuroradiologist, vascular surgeon, sonographer, or the like) does not encounter the calcium shadow, then the plain automated AtheroEdge process as described herein can be run for the IMT measurement.

Figure 5:
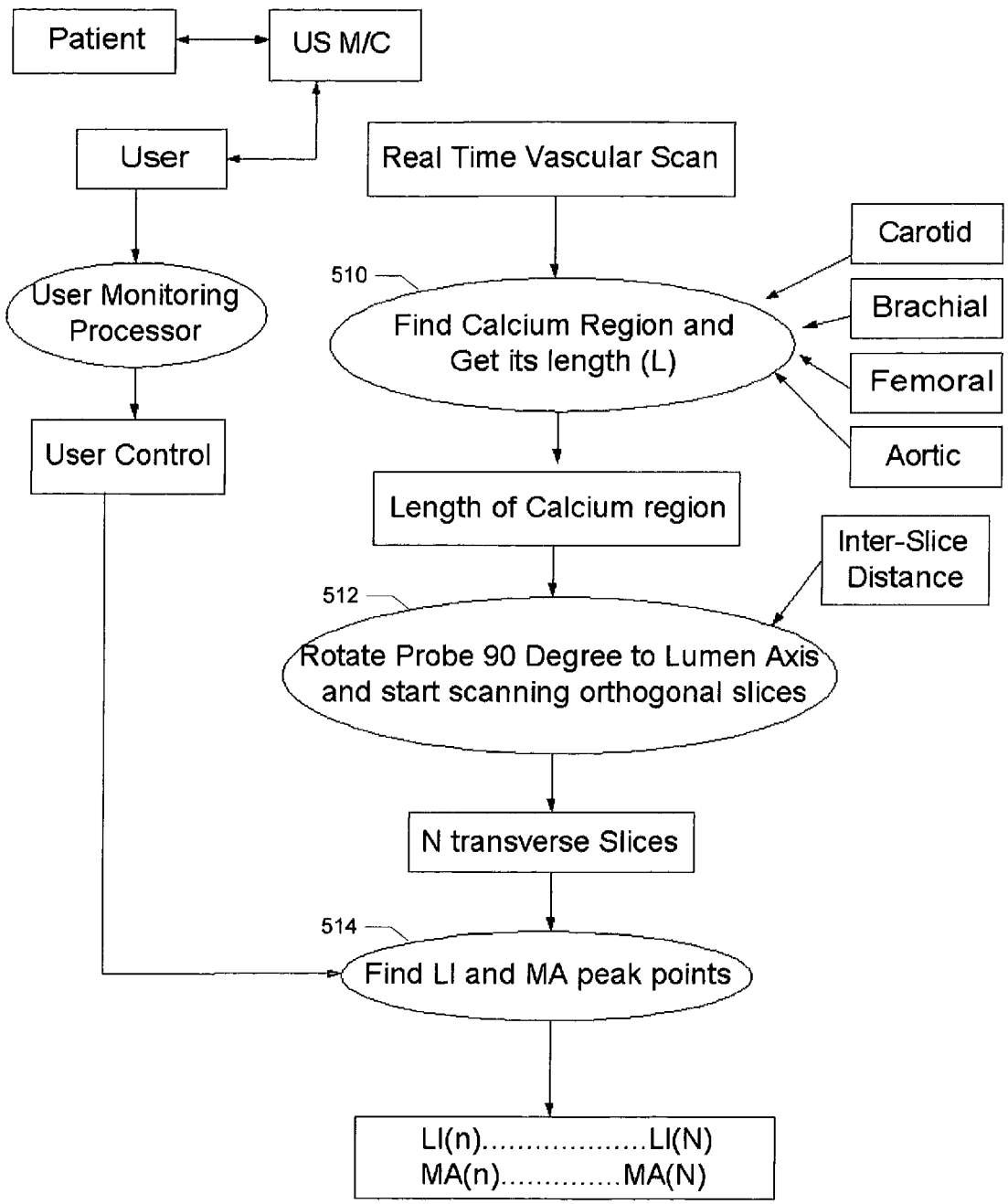
FIG. 5 shows data acquisition when the calcium is found in the proximal (far) wall of the CCA/ICA during the ultrasound scans.

FIG. 5 shows how the system of an example embodiment computes the LI and MA boundaries in the calcium shadow zone, an example of which was shown and described in regard to FIG. 2. The main components of the system of an example embodiment include components to estimate the length of the calcium zone 510, components to acquire the N transverse slices 512, and components to estimate the LI boundary points corresponding to the shadow zone 514. Those of ordinary skill in the art of 3D ultrasound acquisition will notice that the inter-slice distance is important during the scanning process. In our methodology, it is not very critical information as we are only interested in a limited number of points corresponding to the calcium zone.

Figure 6:
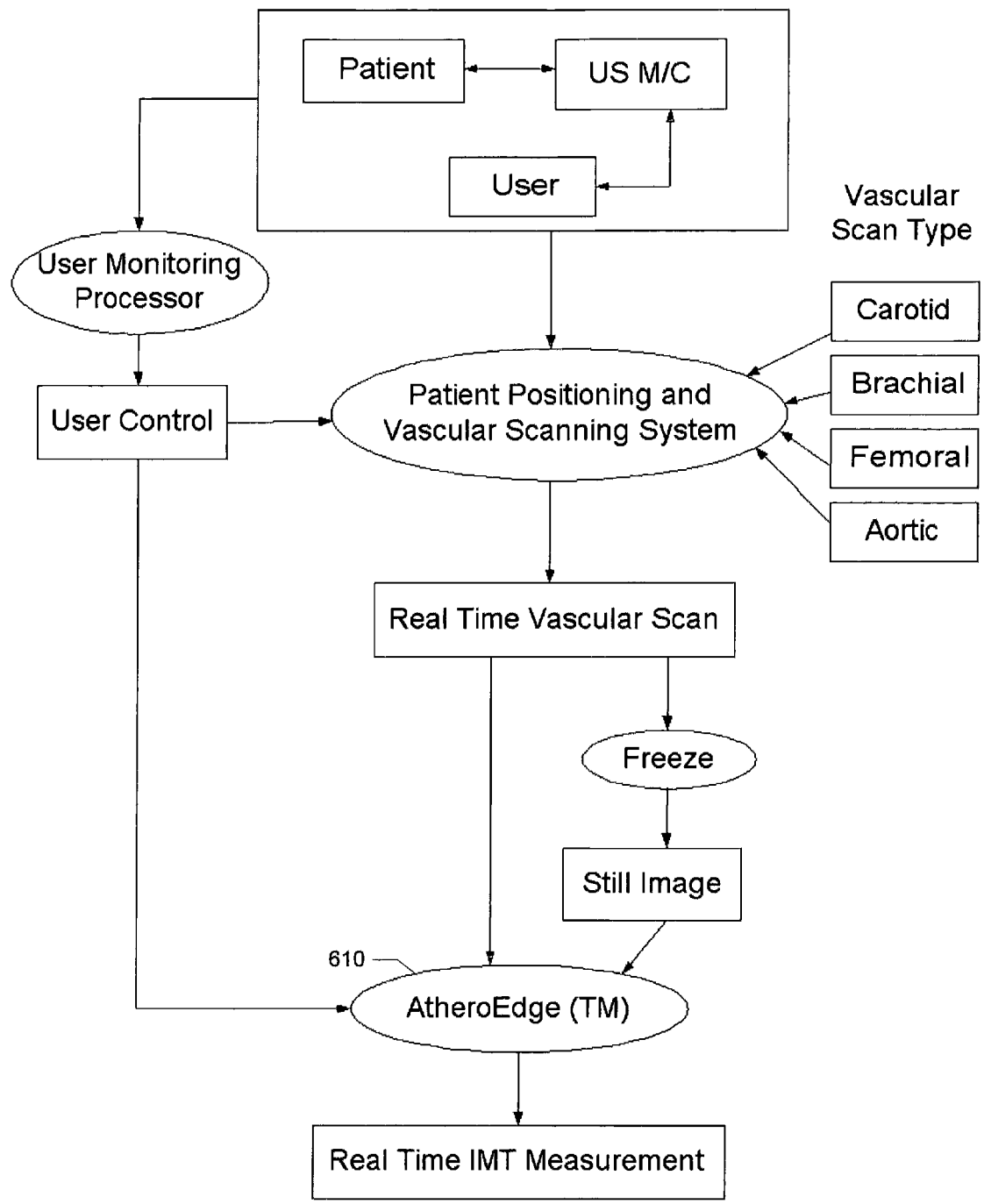
FIG. 6 shows how the AtheroEdge system works given the still image of the B-mode longitudinal image of carotid or how the AtheroEdge system works given the real time image of the B-mode longitudinal image of the carotid artery.

FIG. 6 shows the system of an example embodiment where the AtheroEdge process 610 is being used in normal cases where there is no calcium shadow. The system shows how the ultrasound vascular image is acquired using the longitudinal B-mode process. The input to the system also shows that this process can take data related to any of the four main arteries: carotid, brachial, femoral and aortic. The system has the ability to freeze the image as a still image, on which the IMT can be computed. The user continuously monitors the process at all stages during the operation. The user has control over the AtheroEdge software system of an example embodiment. The user also has control over the ultrasound machine, ultrasound probe, patient and the graphical user interface. The still image can be saved on a hard drive or CD (compact disk) drive. The still image can then also be transferred to an independent computer and the AtheroEdge process 610 can be run on that system as well. At the same time, the AtheroEdge process 610 can run in real-time while the patient is in the vascular screening room.

Figure 7:
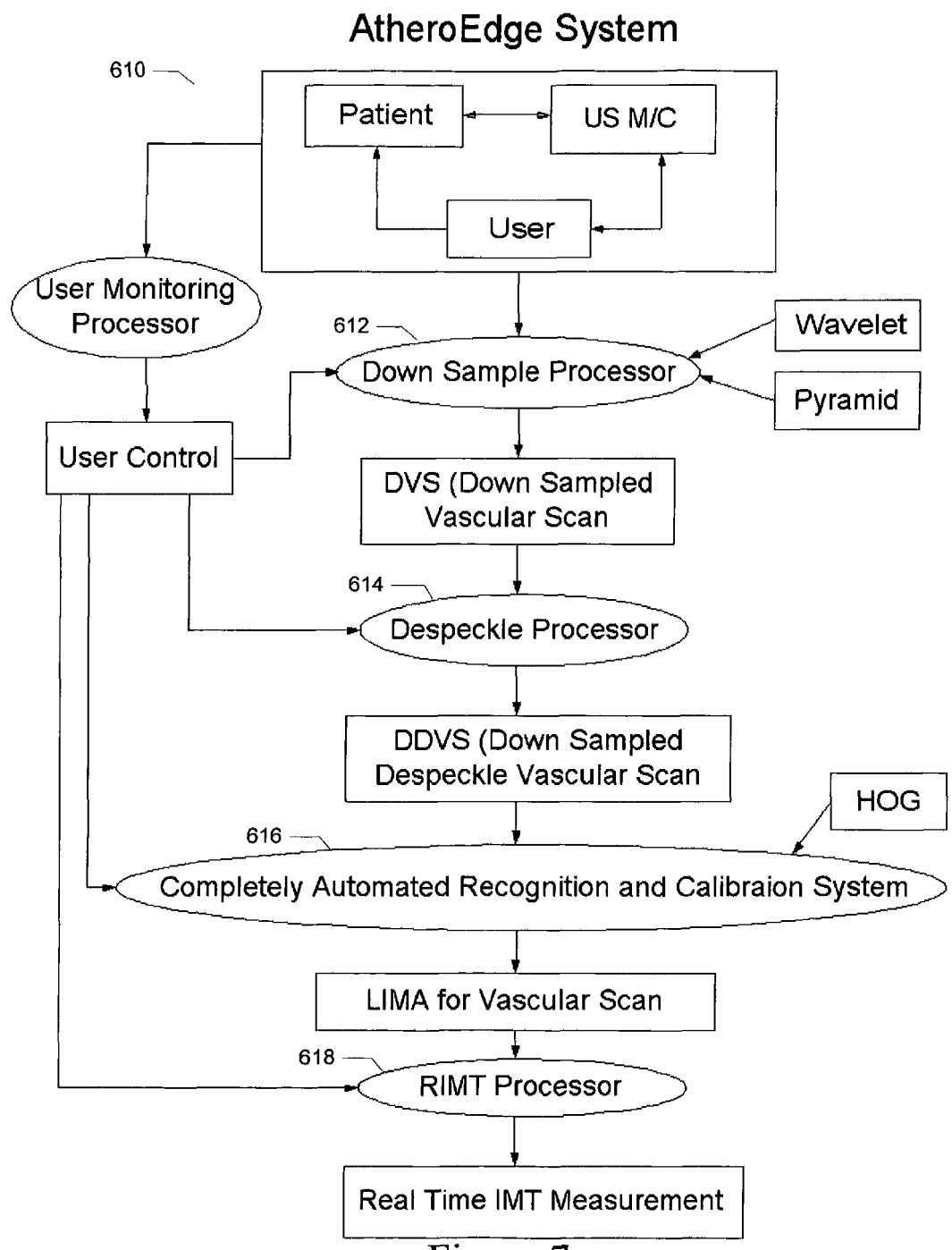
FIG. 7 shows the design of the AtheroEdge system of an example embodiment, which consists of the following sub-systems: (a) down sample or multi-resolution processor; (b) despeckle processor; (c) completely automated recognition processor and calibration system; and (d) RIMT (real-time IMT measurement) processor.

FIG. 7 shows the AtheroEdge system 610 of an example embodiment where the main components of the system include: (a) Multi-resolution Image Processor (also denoted Down Sample Processor) 612; (b) De-speckle Processor 614; (c) Recognition and Calibration Processor 616; and (d) RIMT Processor 618.

Figure 8:
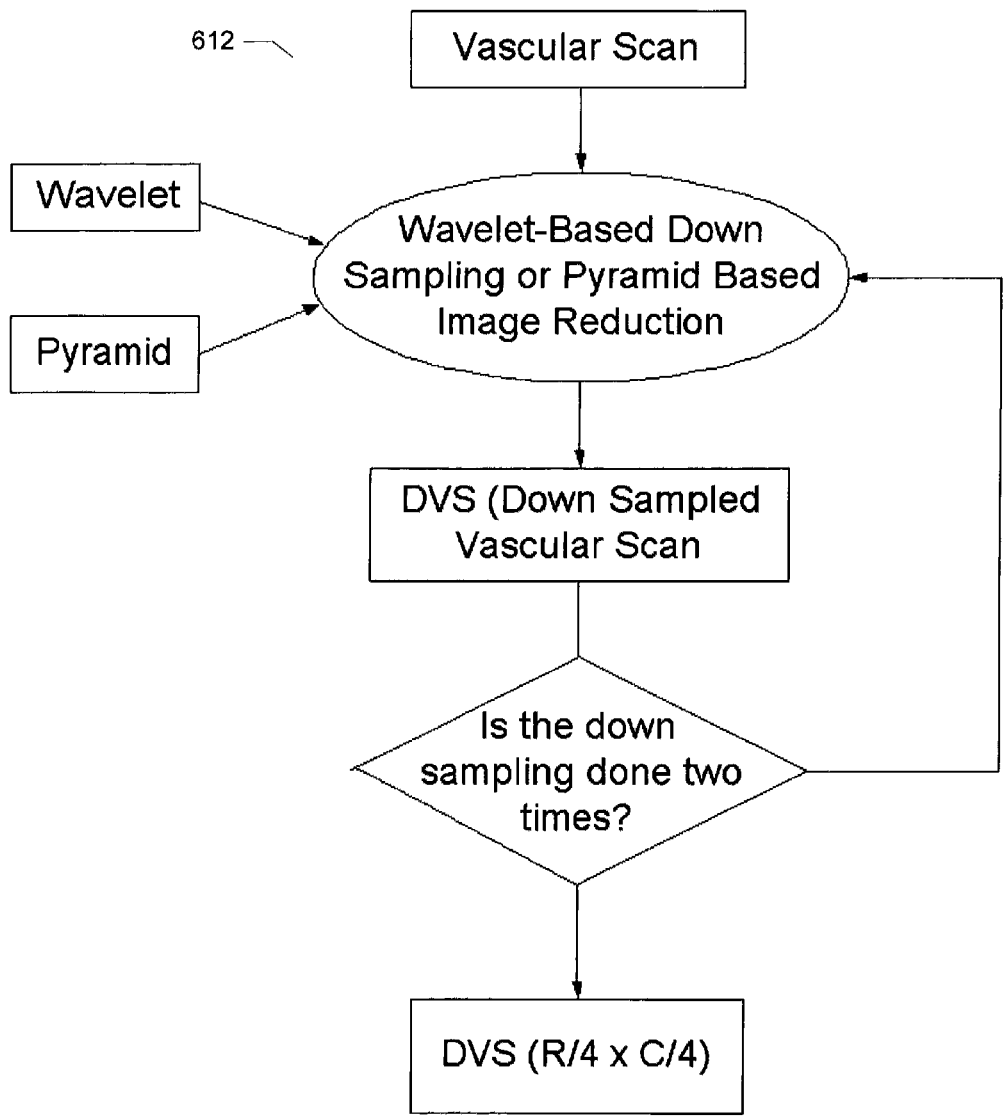
FIG. 8 shows the image reduction processor based on wavelet transform or a pyramid filter, which can down sample the image two or more steps down.

Multi-resolution image processing yields the DSVS (down sampled vascular scan) image. FIG. 8 shows the down sampling or fine to coarse resolution system 612 of an example embodiment. One of four systems can be used for fine to coarse sampling. The role of the multi-resolution process is to convert the image from fine resolution to coarse resolution. Those of ordinary skill in the art of down sampling can use any off-the-shelf down sampling methods. One of the very good down samplers is Lanczos interpolation. This is based on the sinc function which can be given mathematically as:

$$\mathrm{sinc}(x) = \frac{\sin(\pi x)}{\pi x}.$$

Because the sinc function never goes to zero, a practical filter can be implemented by taking the sinc function and multiplying it by a "window", such as Hamming and Hann, giving an overall filter with finite size. We can define the Lanczos window as a sinc function scaled to be wider, and truncated to zero outside of the main lobe. Therefore, the Lanczos filter is a sinc function multiplied by a Lanczos window. A three lobed Lanczos filter can be defined as:

$$Lanczos3(x) = \begin{cases} \dfrac{\sin(\pi x)\sin\left(\pi \dfrac{x}{3}\right)}{\pi x \cdot \pi \dfrac{x}{3}}, & \text{if } |x| \leq 3 \\ 0, & \text{if } |x| > 3 \end{cases}$$

Although Lanczos interpolation is slower than other approaches, it can obtain the best interpolation results; because, the Lanczos method attempts to reconstruct the image by using a series of overlapping sine waves to produce what's called a "best fit" curve. Those of ordinary skill in the art of image down sampling, can also use Wavelet transform filters as they are very useful for multi-resolution analysis. In a particular embodiment, the orthogonal wavelet transform of a signal f can be formulated by:

$$f(t) = \sum_{k \in z} c_J(k)\varphi_{J,k}(t) + \sum_{j=1}^{J} \sum_{k \in Z} d_j(k)\varphi_{j,k}(t)$$

where the $c_j(k)$ is the expansion coefficients and the $d_j(k)$ is the wavelet coefficients. The basis function $\phi_{j,k}(t)$ can be presented as:

$$\phi_{j,k}(t) = 2^{-j/2}\phi(2^{-j}t-k),$$

where k, j are translation and dilation of a wavelet function $\phi(t)$. Therefore, wavelet transforms can provide a smooth approximation of f(t) at scale J and a wavelet decomposition at per scales. For 2-D images, orthogonal wavelet transforms will decompose the original image into four different sub-bands (LL, LH, HL and HH).

Bi-cubic interpolation can also be used, as it will estimate the value at a given point in the destination image by an average of 16 pixels surrounding the closest corresponding pixel in the source image. Given a point (x,y) in the destination image and the point (l,k) (the definitions of l and k are the same as the bilinear method) in the source image, the formulae of bi-cubic interpolation is:

$$f(x, y) = \sum_{m=l-1}^{l+2} \sum_{n=k-1}^{k+2} g(m,n) \cdot r(m-l-dx) \cdot (dy-n+k),$$

where the calculation of dx and dy are the same as the bilinear method. The cubic weighting function r(x) is defined as:

$$r(x) = \frac{1}{6}[p(x+2)^3 - 4p(x+1)^3 + 6p(x)^3 - 4p(x-1)^3],$$

where p(x) is:

$$p(x) = \begin{cases} x & x > 0 \\ 0 & x \leq 0 \end{cases}$$

The bi-cubic approach can achieve a better performance than the bilinear method; because, more neighboring points are included to calculate the interpolation value.

A bilinear interpolator can also be used as it is very simple to implement. Mathematically, a bilinear interpolator is given as: if g represents a source image and f represents a destination image, given a point (x,y) in f, the bilinear method can be presented as:

$$f(x,y)=(1-dx)\cdot(1-dy)\cdot g(l,k)+dx\cdot(1-dy)\cdot g(l+1,k)+(1-dx)\cdot dy\cdot g(l,k+1)+dx\cdot dy\cdot g(l+1,k+1),$$

where $l=\lfloor x \rfloor$ and $k=\lfloor y \rfloor$, and the dx, dy are defined as dx=x−l and dy=y−k respectively. Bilinear interpolation is simple. However, it can cause a small decrease in resolution and blurring because of the averaging nature of the computation.

Figure 9:
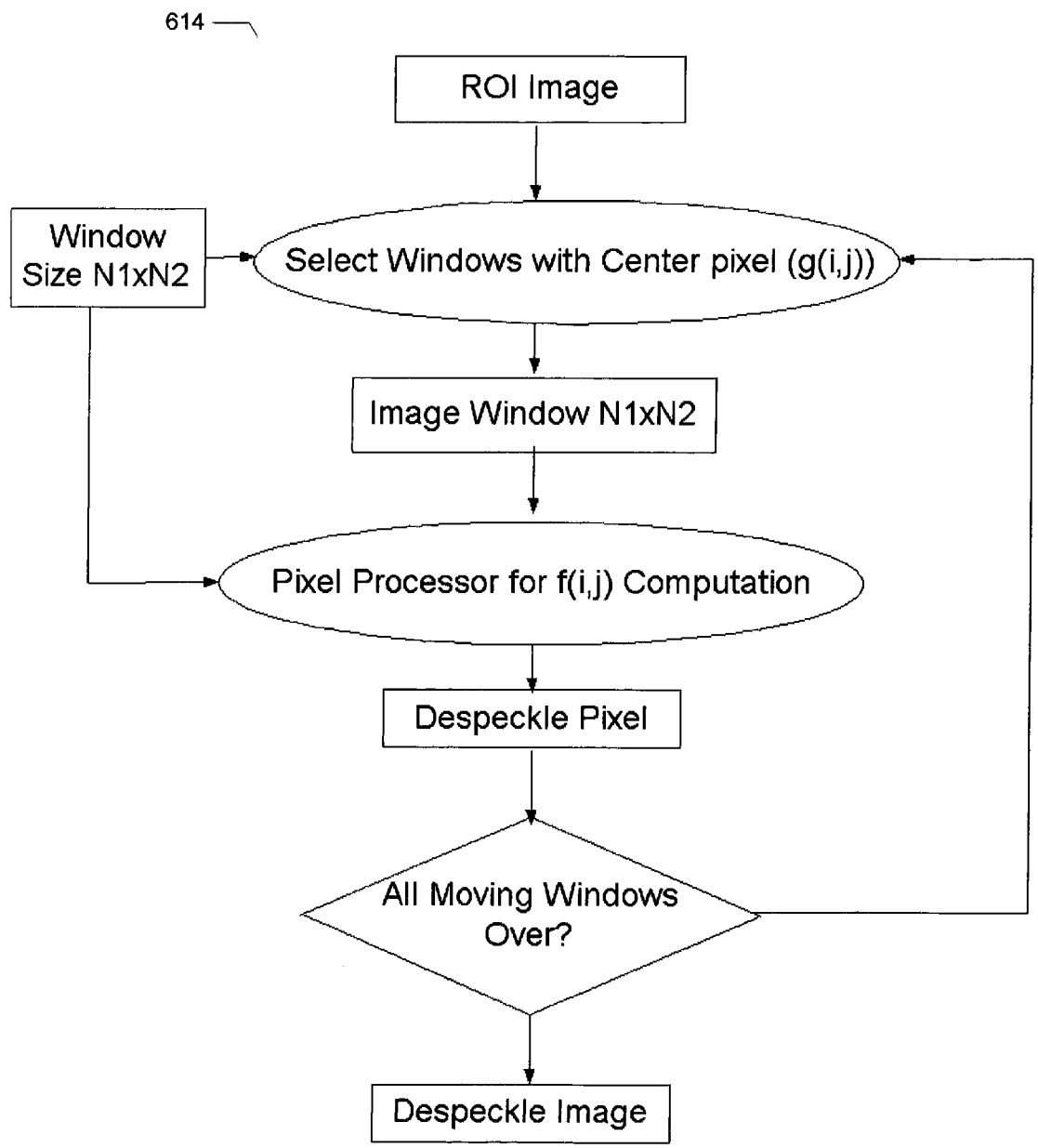
FIG. 9 shows the despeckle processor, which removes the speckles in the ultrasound region of interest. A moving window method is used in a particular embodiment for implementing the de-speckle filtering process.
Figure 10:
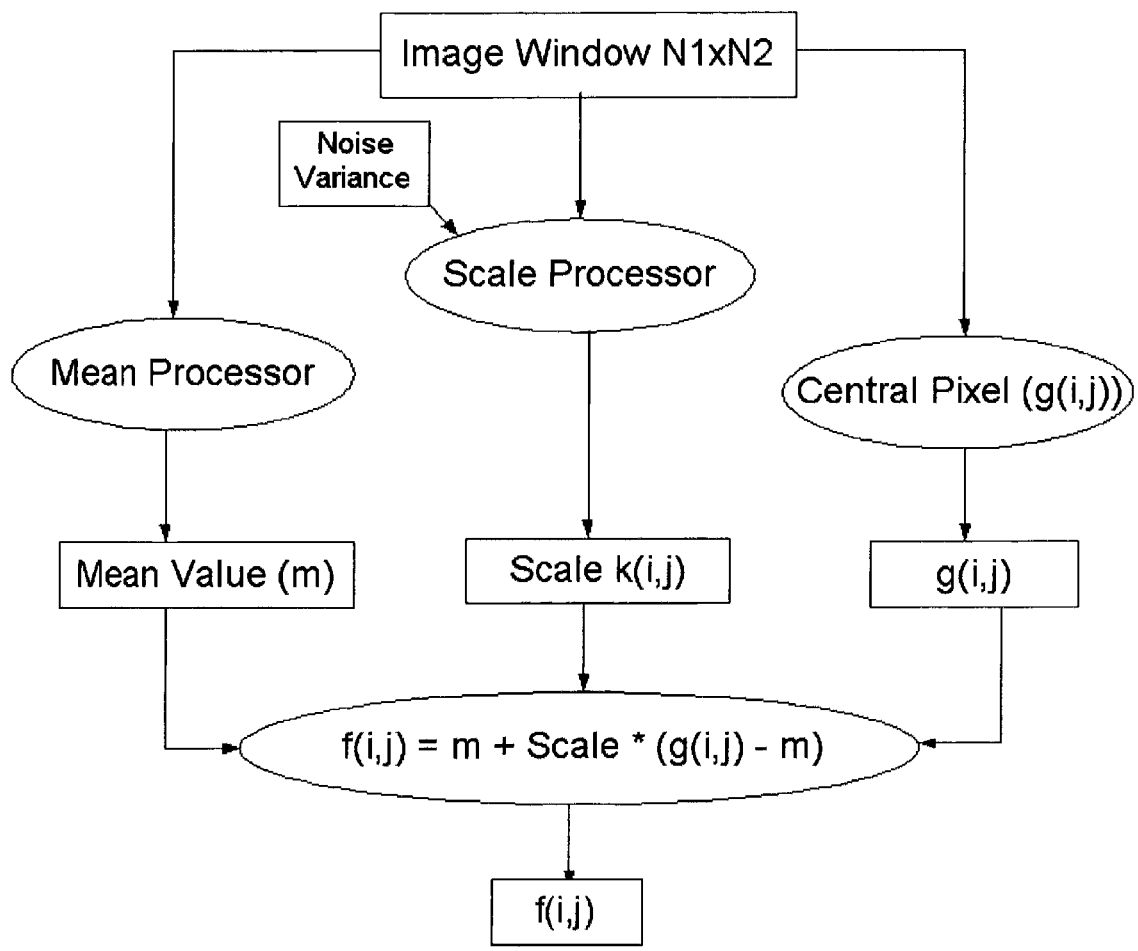
FIG. 10 shows the process for computing the de-speckle pixel and replacing the original noisy pixel with the de-speckle pixel. The process uses the scaling of the original pixel. The noise variance process is being used by the scale processor.
Figure 11:
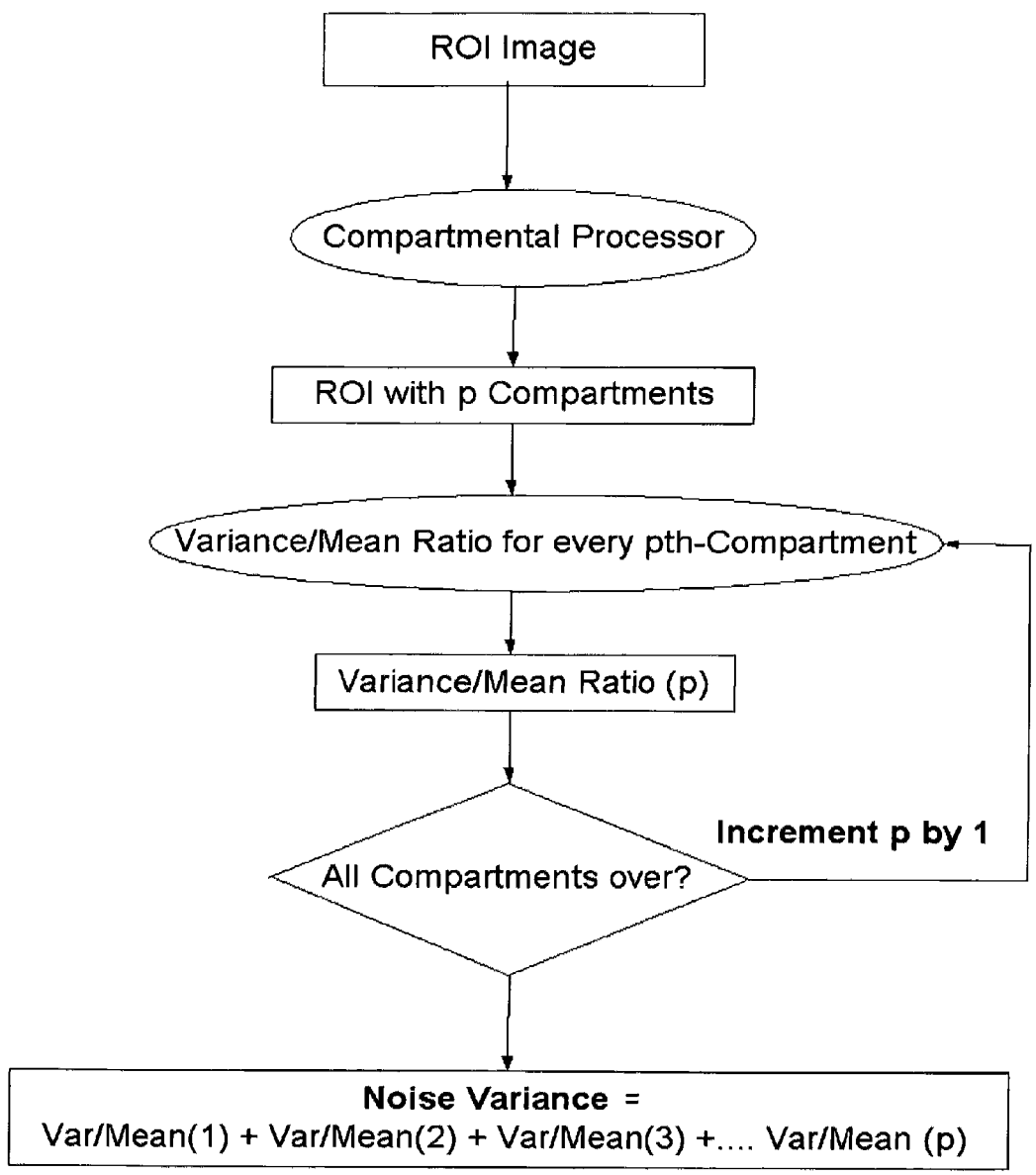
FIG. 11 shows the computation of the noise variance processor. The noise variance is computed by summing the variance to mean ratios for all the compartments of the ROI region.

FIGS. 9, 10 and 11 describe the de-speckle filtering component 614 of an example embodiment; whose output is a DDVS (Down sampled Despeckle Vascular Scan). Speckle noise was attenuated by using a first-order statistics filter, which gave the best performance in the specific case of carotid imaging. This filter is defined by the following equation:

$$J_{x,y}=\bar{I}+k_{x,y}(I_{x,y}-\bar{I}) \quad (1)$$

where, $I_{x,y}$ is the intensity of the noisy pixel, $\bar{I}$ is the mean intensity of a N×M pixel neighborhood and $k_{x,y}$ is a local statistic measure. The noise-free pixel is indicated by $J_{x,y}$. $k_{x,y}$ is mathematically defined as:

$$k_{x,y} = \frac{\sigma_I^2}{\bar{I}^2 \sigma_I^2 + \sigma_n^2},$$

where $\sigma_I^2$ the variance of the pixels in the neighborhood, and $\sigma_n^2$ the variance of the noise in the cropped image. An optimal neighborhood size in an example embodiment can be 7×7 pixels. Note that the despeckle filter is useful in removing the spurious peaks, if any, during the adventitia identification in subsequent steps. Those of ordinary skill in the art can use any local statistical noise removal filter or filters based on morphological processing or filters presented in Suri et al., MODELING SEGMENTATION VIA GEOMETRIC DEFORMABLE REGULARIZERS, PDE AND LEVEL SETS IN STILL AND MOTION IMAGERY: A REVISIT, International Journal of Image and Graphics, Vol. 1, No. 4 (2001) 681-734.

Figure 12:
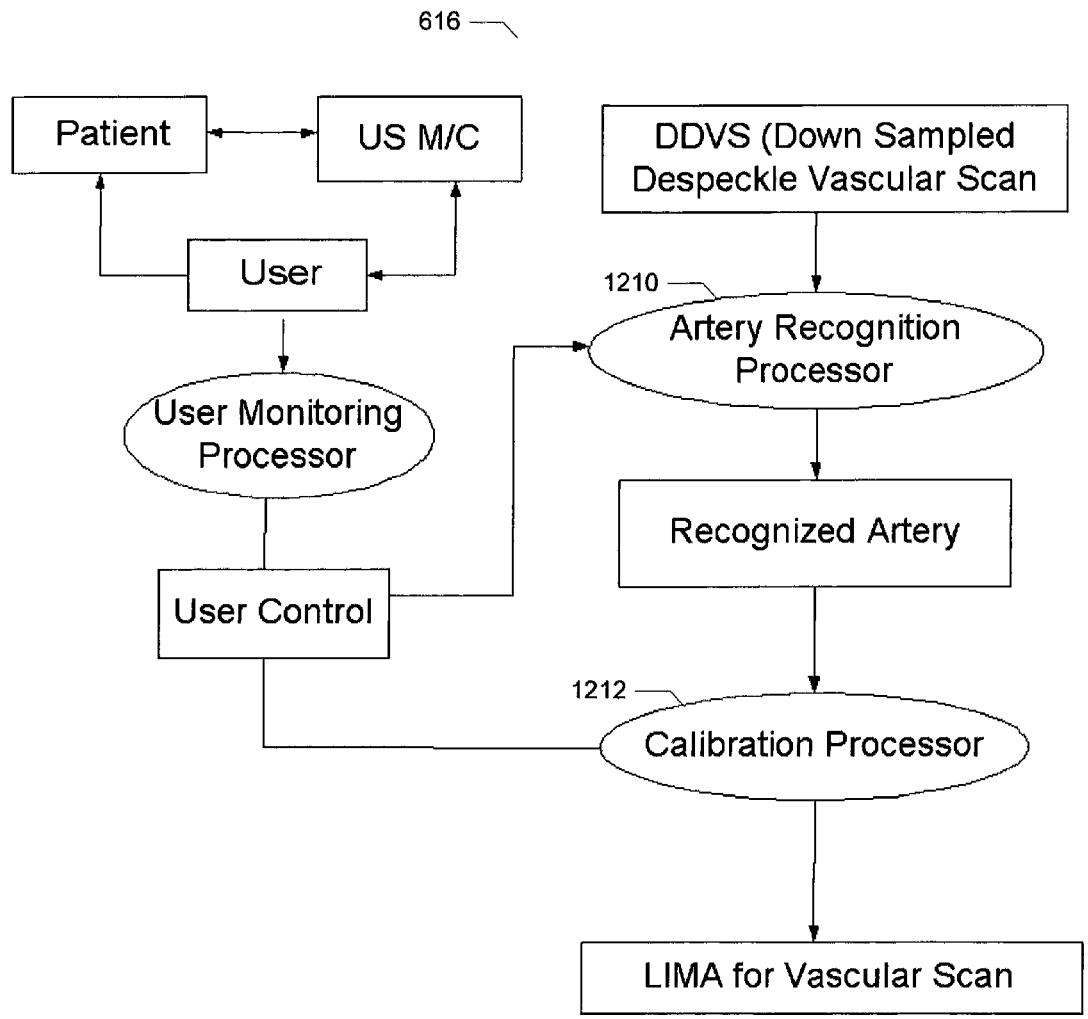
FIG. 12 shows the joint recognition and calibration processor for computing the LIMA borders after the automated recognition process. Calibration phase is definite phase for any LIMA borders to be estimated along with the IMT values.

FIG. 12 shows the last and the final stage in an example embodiment as the recognition and calibration system 616 shown in the process called "Completely Automated Recognition and Calibration Processor". While the two stages 1210 and 1212 are cascaded and shown to be different blocks, this arrangement is transparent to the user. This means the software is cascading information from one block to another block without user interaction. The user still has full control and user monitoring is fully active and the user can interrupt the system at any time.

Figure 13:
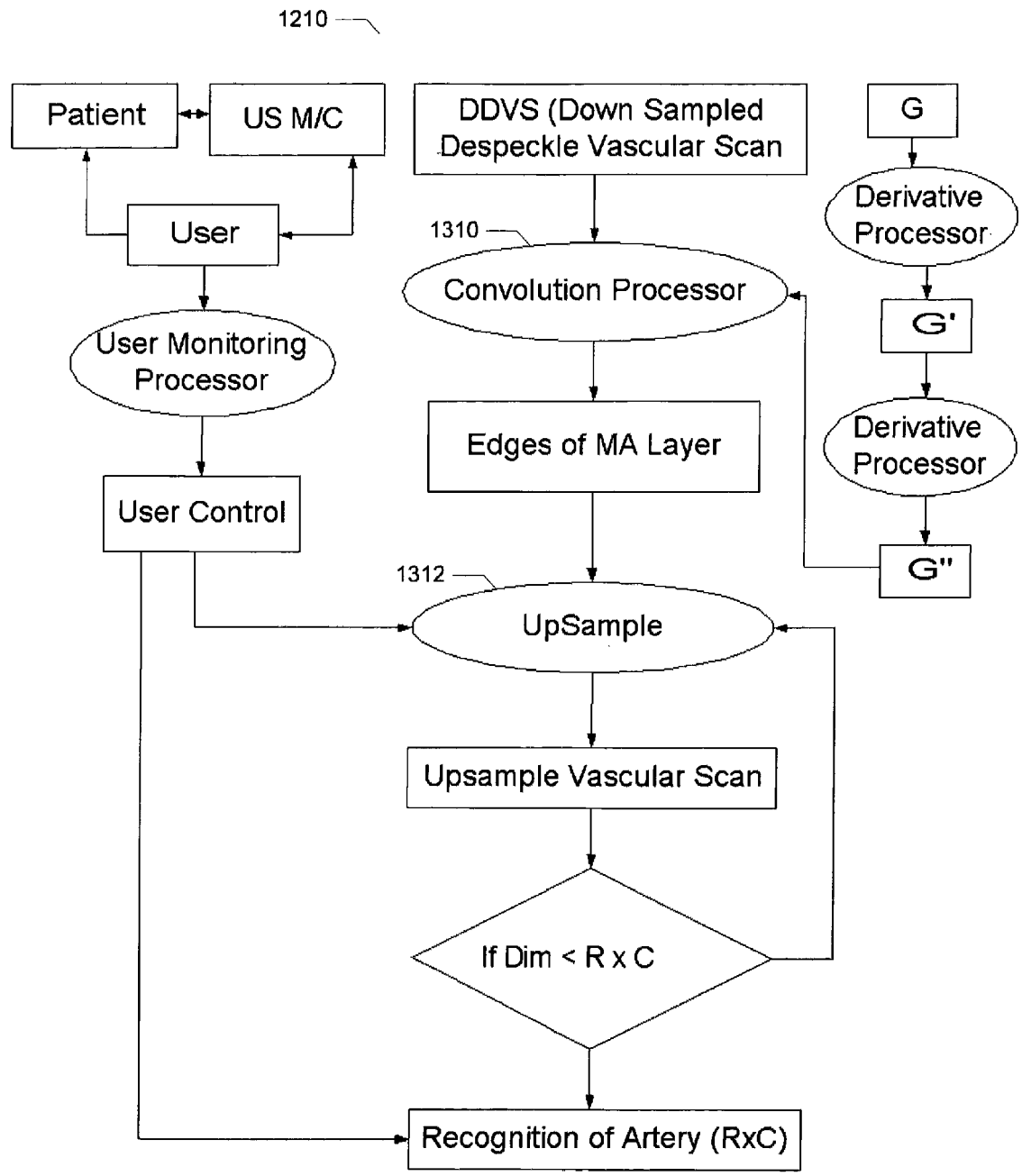
FIG. 13 shows the artery recognition process of an example embodiment, where the input image is the down sampled image of the cropped image.

FIG. 13 shows the Artery Recognition Processor 1210, which represents a novel aspect of an example embodiment, as the Artery Recognition Processor 1210 performs the automated recognition of an artery. The Artery Recognition Processor 1210 of an example embodiment has two stages: (a) a convolution and heuristic processor 1310, and (b) an up-sample or up-sampling processor 1312.

The convolution processor 1310 is used for convolution of the first order derivative G with the despeckled image. The scale parameter of the Gaussian derivative kernel was taken equal to 8 pixels, i.e. to the expected dimension of the IMT value. In fact, an average IMT value of say 1 mm corresponds to about 16 pixels in the original image scale and, consequently, to 8 pixels in the coarse or down sampled image. The convolution processor 1310 outcome will lead to the clear information for the near and far vessel walls. This information will have two parallel bands corresponding to the far and near vessel walls. These bands will follow the curvature of the vessel walls. If the vessel wall is oriented downwards or upwards or has a bending nature, the bands will follow on both sides of the lumen. These bands have information which corresponds to the maximum intensity saturated to the maximum values of 2 powers 8, the highest value. For an 8 bit image, this value will be 255.

The convolution process then allows the heuristics to estimate the Far Adventitia borders of the far wall or near wall. To automatically trace the profile of the far wall, we used a heuristic search applied to the intensity profile of each column. In a particular embodiment, we use an image convention wherein (0,0) is the top left hand corner of the image. Starting from the bottom of the image (i.e., from the pixel with the higher row index), we search for the first white region constituting at least 6 pixels of width. The deepest point of this region (i.e., the pixel with the higher row index) marked the position of the far adventitia ($AD_F$) layer on that column. The sequence of points resulting from the heuristic search for all the image columns constitutes the overall automated far wall adventitia tracing $AD_F$.

The last stage of the Artery Recognition Processor 1210 is the up-sampling processor 1312, which allows the adventitia tracing $AD_F$ to be up-sampled back to the original scale of cropped image. The $AD_F$ profile was then up-sampled to the original scale and superimposed over the original cropped image for both visualization and determination of the region of interest for the segmentation (or calibration) phase. At this stage, the CA far wall is automatically located in the image frame and automated segmentation is made possible.

This Artery Recognition Processor 1210 (stage I) is an innovative aspect of our methodology. The Artery Recognition Processor 1210 consists of a superior architecture based on fine to coarse sampling for vessel wall scale reduction, speckle noise removal, and higher-order Gaussian convolution, and automated recognition of Adventitia. The ability of the segmentation or calibration phase (stage II) to be guided by the automated CA wall recognition process is in itself another innovative aspect of our methodology. The first-order Gaussian kernel convolution allows for efficient detection of the CA walls. This kernel has unitary energy. When such kernel is located in proximity of a neat gray level change, it enhances the transition. Consequently, the most echoic image interfaces are enhanced to white in the filtered image. For this reason, the Artery Recognition Processor 1210 allows for detecting the adventitia layer.

Figure 14:
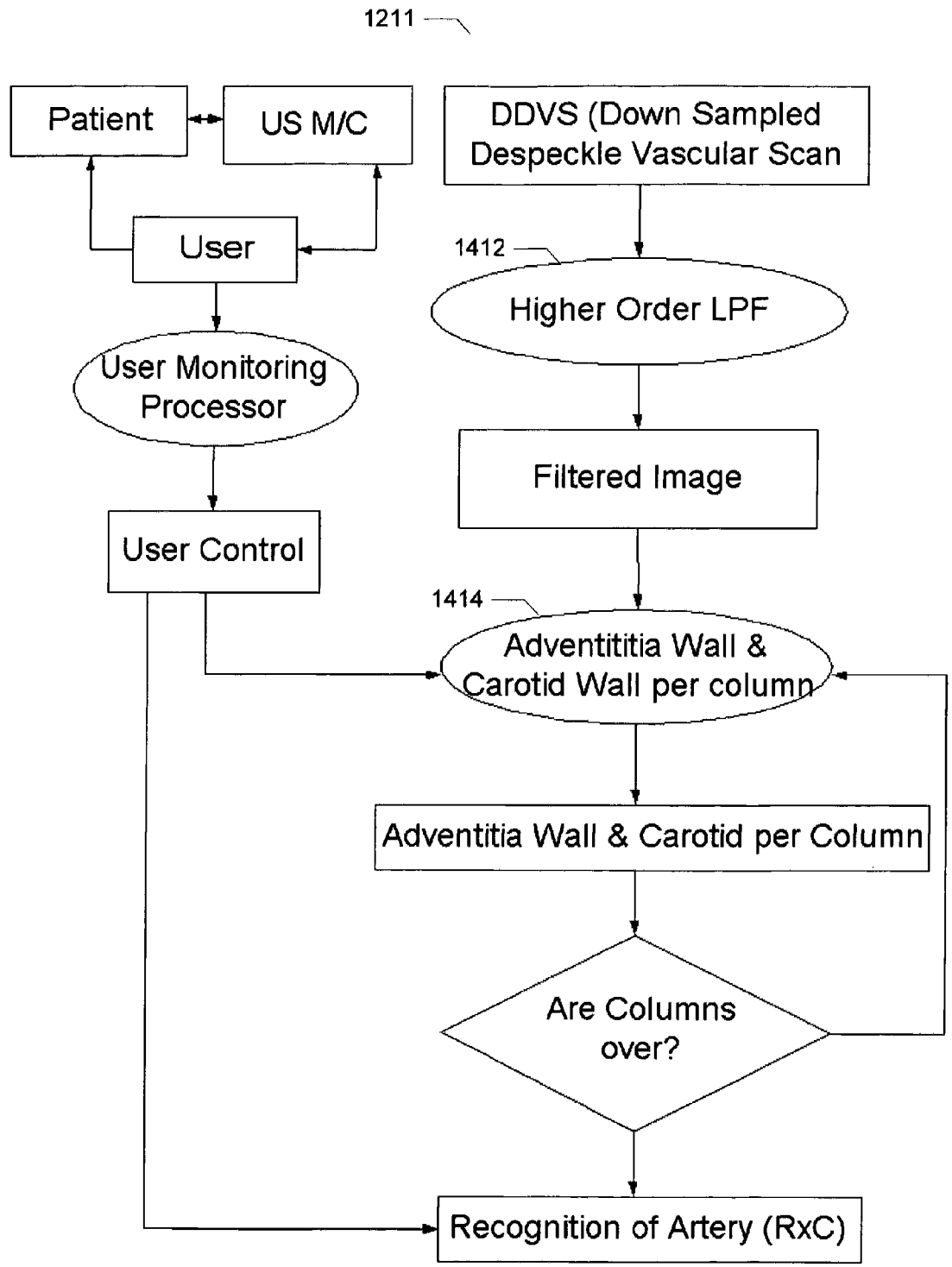
FIG. 14 shows an alternative Artery Recognition Processor based on the combination of an LPF component and a Peak Detection component in an example embodiment.

Those of ordinary skill in the art in view of this disclosure can make another combination of the Artery Recognition Processor 1210 and a calibration system 1212; for example, FIG. 14 shows another Artery Recognition Processor 1211 based on the combination of an LPF component 1412 and a Peak Detection component 1414. This Artery Recognition Processor 1211 can also be connected to the calibration system (stage-II) 1212. This Artery Recognition Processor 1211 has several advantages to it:

(1) Robustness and Accurate Wall Capture: Artery Recognition Processor 1211 is very robust because the higher order derivative kernels are very good in capturing the vessel walls (see, A Review on MR Vascular Image Processing Algorithms: Acquisition and Pre-filtering: Part I, Suri et al., IEEE TRANSACTIONS ON INFORMATION TECHNOLOGY IN BIOMEDICINE, VOL. 6, NO. 4, pp. 324-337, DECEMBER 2002; and A Review on MR Vascular Image Processing:Skeleton Versus Nonskeleton Approaches: Part II, Sufi et al., *IEEE TRANSACTIONS ON INFORMATION TECHNOLOGY IN BIOMEDICINE*, VOL. 6, NO. 4, DECEMBER 2002).

(2) Faster than the conventional processing: Because the recognition is strategized at a coarse resolution level down sampled twice from its original size of the image, it is therefore processing $\frac{1}{4}^{th}$ the number of pixels for automated recognition of the media layer. This improves the speed and throughput of the system.

(3) Independent of Orientation of the vascular scan: Another major advantage to the system is that these Gaussian kernels are independent of the orientation of the blood vessels in the image. Because the ultrasound vascular scans do not always have the vessel orientation horizontal with respect bottom edge of the image, manual methods can pose a further challenge in regard to the region of interest estimation.

(4) Guiding Method for the Calibration System: Because the recognition process is followed by the calibration process, the calibration system becomes very robust; because, the calibration processing is done in the region of interest determined by the automated recognition system. Thus, the calibration system adds the value determined by the automated recognition system for vascular ultrasound, such as IMT measurement for carotid, femoral, aortic and brachial. Such a combination where the calibration system is guided by the automated recognition system helps in mass processing of huge databases of medical images.

(5) Running the Mass IMT system for Clinical Analysis: Because the recognition process is automated and followed by the calibration process, an important benefit such a system can deliver is in its real time use for analysis of IMT measurement on large databases. Running clinical databases on still images is even more beneficial; because, such a system is completely automated in terms of recognition and IMT measurement.

(6) Applications: Because the ultrasound probes use almost the same frequency of operation for scanning the vascular arteries such as carotid, femoral, brachial and aortic, it is thus possible to use such a system for these blood vessels.

Figure 15:
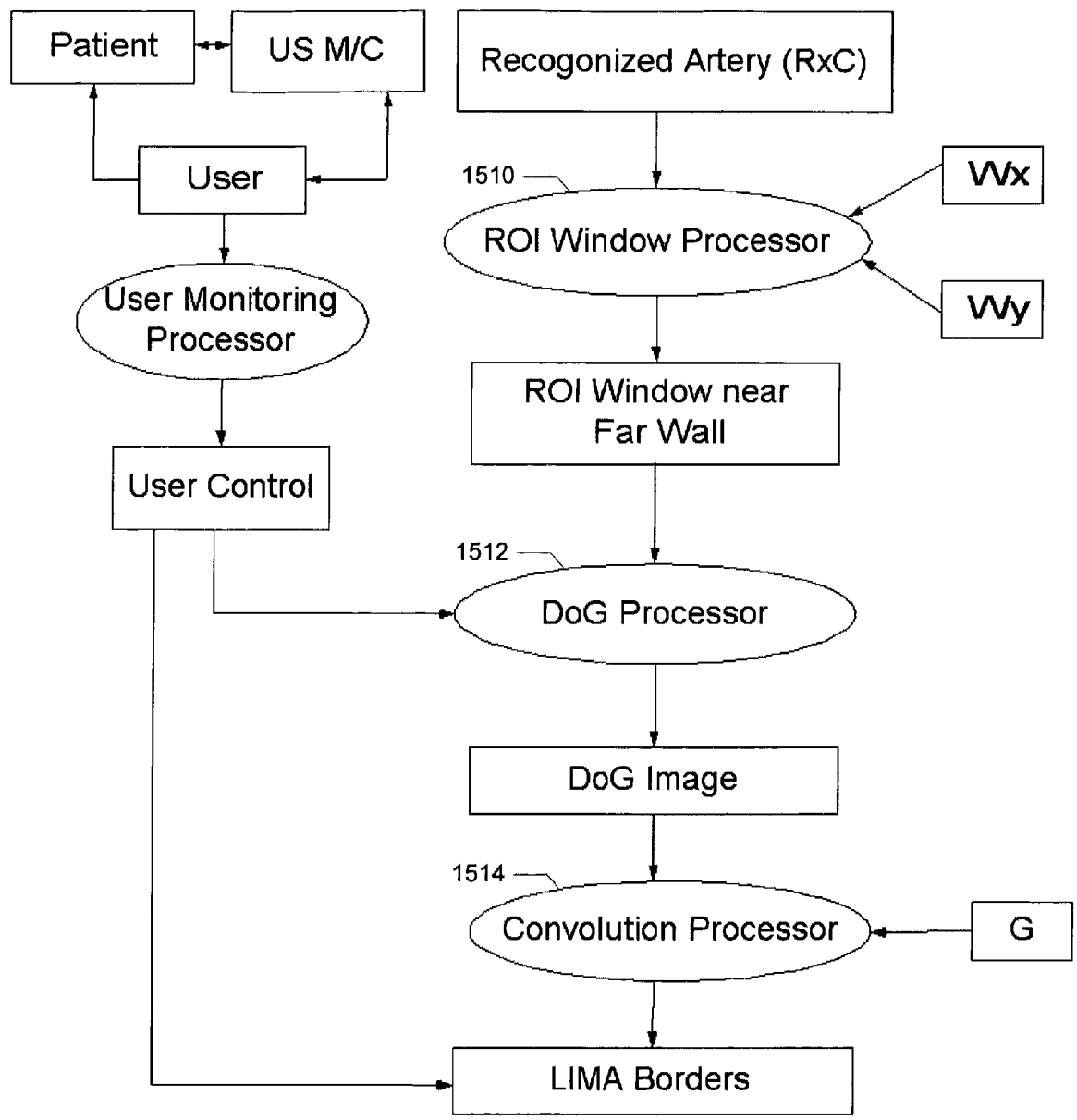
FIG. 15 shows the calibration processor. An example embodiment of the calibration processor includes three processors: (a) sub-ROI processor; (b) DoG (Difference of Gaussian) processor and (c) convolution processor. The sub-ROI is generated by giving a pre-defined ROI (region of interest) given the recognized MA border. DoG (Difference of Gaussian) process is computed by taking the difference of the Gaussian kernels. The Convolution process is computed by taking the convolution of the Gaussian kernel with the DoG image.

FIG. 15 shows the domain based calibration process or segmentation processor 1212. The system of an example embodiment is divided into three components: (a) Guidance Zone Processor (also denoted the ROI Window processor) 1510; (b) DoG (Difference of Gaussian) Filtering Processor 1512; and (c) Heuristic Processor (also denoted Convolution processor) 1514. Because the Artery Recognition Processor 1210 has identified the adventitia tracing $AD_F$, the calibration needs to be applied in the zone which was initially guided by the Artery Recognition Processor 1210. Because the calibration stage is a combination of finding the edges of the LI and MA borders, the importance of the guidance zone is very crucial. The Guidance Zone is the key to avoid the false peaks estimation in the calibration phase.

Figure 18B:
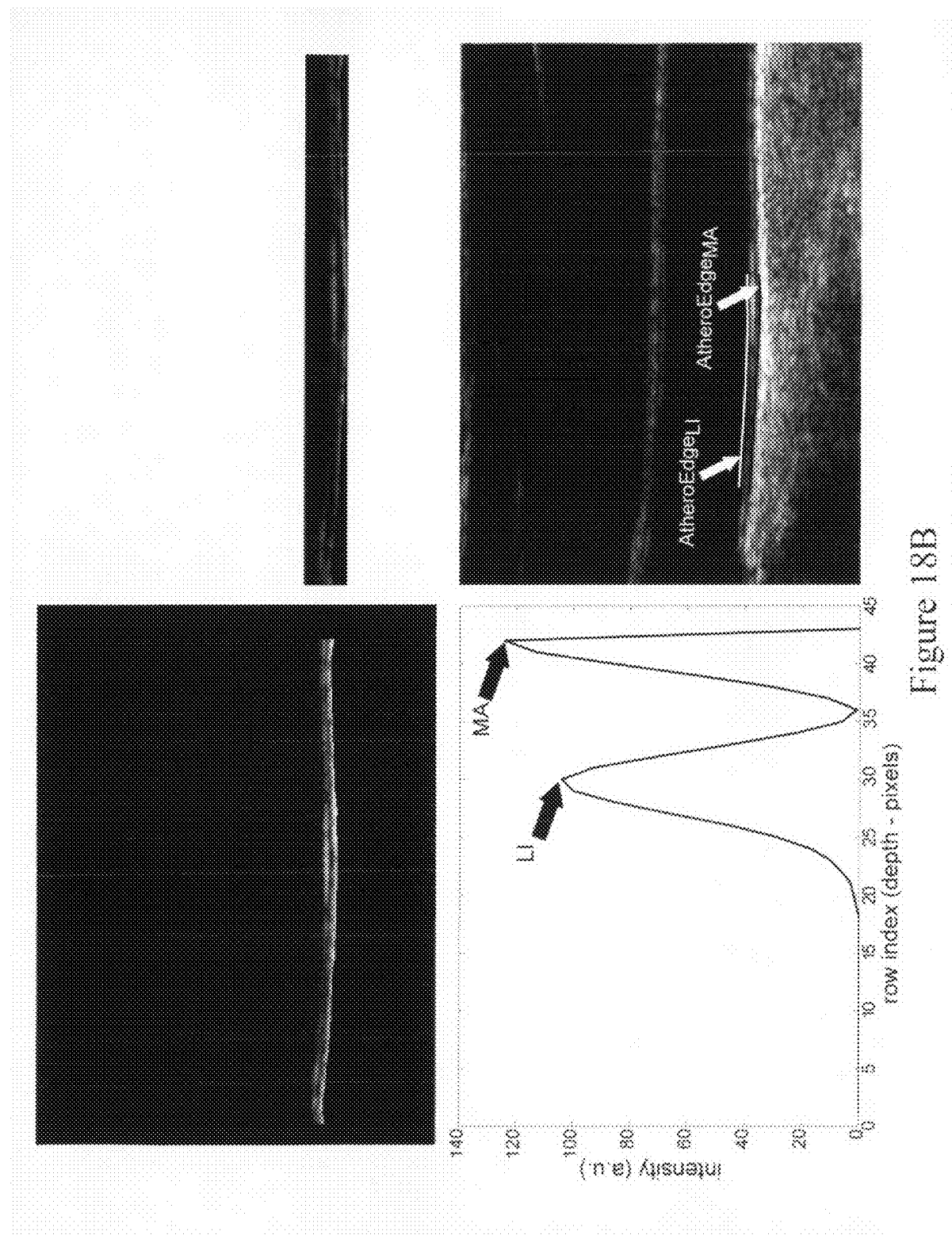
FIG. 18B shows sample images of the region of interest (ROI) for an example embodiment.

The Guidance Zone is built around the adventitia tracing $AD_F$. The Guidance Zone is a region-of-interest (ROI) around the automatically traced $AD_F$ profile, also denoted the domain region, in which the segmentation will run. The ROI is designed such that it has the same width as the $AD_F$ curve. This will allow the creation of the largest possible ROI, according to the detected length of the adventitia layer. For example, the height in a particular embodiment is equal to 30 pixels (1.8 mm for images with 16.67 pixels/mm of density, and 1.875 mm for images with 16 pixels/mm of density). For each point of the $AD_F$ profile we considered as an upper limit of the ROI the pixel with a row index of 30 pixels lower, towards the upper edge of the cropped image. Substantially, the bottom limit of the ROI was the $AD_F$ curve while the upper limit was $AD_F$ shifted by 30 pixels. FIG. 18B shows the ROI (depicted in the original image scale) for an example embodiment.

The second step of the calibration phase is the DoG filtering performed by DoG Filtering Processor 1512. In an example embodiment, an MRAFOAM (Multi-resolution First Order Absolute Moment) operator is used for final segmentation of LI and MA borders in the automatically determined guidance zone (see Demi et al., *The First Absolute Central Moment in Low-Level Image Processing, Computer Vision and Image Understanding*, Vol. 80, pp. 57-87, 2000) for the DoG Filtering and edge detection based on First Absolute Central Moment Filter. The filter can also be applied to ultrasound images (see, Faita F, Gemignani V, Bianchini E, Giannarelli C, Ghiadoni L, Demi M *Real-time measurement system for evaluation of the carotid intima-media thickness with a robust edge operator. J Ultrasound Med.* 2008; 27:1353-61). The edge information is mathematically given as:

$$e(x, y) = \frac{1}{A_\theta} \int \int_\theta |I_1(x, y) - I_2(x - x', y - y')| \cdot G(x, y, \sigma) dx' dy' \qquad (2)$$

where $I_1(x,y)=I(x,y)\otimes G(x,y,\sigma_1)$ and $I_2(x,y)=I(x,y)\otimes G(x,y,\sigma_2)$ are computed by low-pass filtering the input image $I(x,y)$ by a Gaussian kernel with standard deviations equal to $\sigma_1$ and $\sigma_2$, respectively. This low-pass filtering step is required in order to cope with images having low values of signal-to-noise. The subtraction term in eq. (2)

above is the Difference of Gaussian (DoG) operator. The third Gaussian kernel $G(x,y,\sigma_r)$ is a regularization and weighting term. The '·' sign in eq. (2) above indicates the bi-dimensional convolution (i.e. filtering) by the kernel $G(x,y,\sigma_r)$. When computed in a homogeneous region, the MRAFOAM operator $e(x,y)$ is zero valued. When computed in the presence of a gray level discontinuity, the value of $e(x,y)$ increases. In our MRAFOAM for a particular embodiment, we used $\sigma_1 = \sigma_r = 0.3$ mm and $\sigma_2$ equal to 0.6 mm.

The last stage of the calibration processor 1212 is the Heuristic Processor 1514 for LIMA border estimation. The LI and MA interfaces are searched by relying on a heuristic search. The Heuristic Processor 1514 uses the information along a single grayscale column across the longitudinal axis of the carotid scan or vascular artery. These grayscale columns are also called profiles; because, each column is a signature of the intensities along the column. Because the Guidance Zone is so accurately determined in a multi-resolution approach as guided by the Artery Recognition Processor 1210, the signature will show only two peaks—one corresponding to the LI border and a second peak corresponding to the MA border. These two high intensity peaks of the MRAFOAM signature can be automatically marked. Because there are two peaks, it is easy to identify which peak is the highest. This highest peak is called MRAFOAM-MAX$_1$ and is the MA border. This can be called local maxima along the signature guided by the multi-resolution Artery Recognition Processor 1210. The second local maxima, MRAFOAM-MAX$_2$, are searched in the neighborhood of MRAFOAM-MAX$_1$, such that MRAFOAM-MAX$_2 \geq \beta \times$ MRAFOAM-MAX$_1$, where, $\beta$ is 0.1 or 10%, determined empirically from the database. This second peak is called MRAFOAM-MAX$_2$ and is the LI border. Those of ordinary skill in the art in view of this disclosure will notice that the deepest row maximum is being assigned to the MA while the uppermost row maximum is being assigned to the LI. Also, those of ordinary skill in the art in view of this disclosure can replace the search strategy by Dynamic Programming for the Calibration stage, as consistent with the techniques described herein. The Heuristic Processor 1514 can be applied to all the columns one-by-one to produce the MA and LI border points along the B-mode Guidance Zone.

Performance Metric: The segmentation errors can be computed by comparing automated tracings by the AthreoEdge system as described herein with manual segmentations. As described above, the AtheroEdge process of an example embodiment includes two steps: (i) the automated recognition of the carotid artery (CA) in the image frame, and (ii) the segmentation of the far CA wall. The automatically traced LI and MA profiles can be used to measure the IMT. For performance measuring, we used the Polyline Distance measure (PDM) as a performance metric. A detailed description of the PDM can be found in the prior art. By way of summarizing PDM, given two boundaries $B_1$ and $B_2$, first the distance of the vertices of a boundary $B_1$ from the segments of the boundary $B_2$ is computed. Then, the dual distance (i.e. the distance of the vertices of $B_2$ from the segments of $B_1$) is computed. The final PDM measure is the average distance of the two distances normalized to the overall number of points (i.e., the sum of the points of $B_1$ and $B_2$). It was proven that PDM is almost independent of the number of points of the boundaries. Hence, PDM is proposed as a good metric when used in the presence of boundaries with a different number of points. For example, in our dataset, the manual profiles had an average number of points of 20, whereas the computer generated boundaries had an average number of points equal to about 250.

Considering the i-th image of the dataset, the segmentation errors for the LI and MA boundaries were defined as:

$$\epsilon^i_{LI} = PDM(\text{AtheroEdge}_{LI}, GT_{LI})$$

$$\epsilon^i_{MA} = PDM(\text{AtheroEdge}_{MA}, GT_{MA}) \quad (3)$$

Where, AtheroEdge$_{LI}$ and AtheroEdge$_{MA}$ are the LI and MA profiles traced by AtheroEdge, and $GT_{LI}$ and $GT_{MA}$ are the ground-truth boundaries. Analogous errors were defined for AtheroEdge boundaries. The mean LI and MA performance was computed as:

$$\left. \begin{array}{l} \bar{\epsilon}_{LI} = \dfrac{1}{N} \sum_i \epsilon^i_{LI} \\ \bar{\epsilon}_{MA} = \dfrac{1}{N} \sum_i \epsilon^i_{MA} \end{array} \right\} \quad (4)$$

where N is the total number of images of the testing database.

For performance evaluation, we compare the AtheroEdge process as described herein with the published data by an automated IMT measurement system called CALEX described in a publication (Molinari F, Zeng G, Suri J S. (*CALEX*)—*An integrated approach to computer-based automated tracing and its validation for* 200 *common carotid arterial wall ultrasound images: A new technique. J Ultras Med.* 2010; 29:399-418).

The IMT value was computed as the distance between the LI and the MA profiles on every single image. Therefore, for every image, we computed an IMT value for AtheroEdge (called AtheroEdge$_{IMT}$), for CALEX (called CALEX$_{IMT}$) and for ground-truth (GT$_{IMT}$). The IMT measurement bias was defined as:

$$\mu^i_{AtheroEdge} = |\text{AtheroEdge}^i_{IMT} - GT^i_{IMT}|$$

$$\mu^i_{CALEX} = |\text{CALEX}^i_{IMT} - GT^i_{IMT}| \quad (5)$$

The overall system performance of the system in terms of IMT measurement was computed as:

$$\left. \begin{array}{l} \bar{\mu}_{AtheroEdge} = \dfrac{1}{N} \sum_i \mu^i_{AtheroEdge} \\ \bar{\mu}_{CALEX} = \dfrac{1}{N} \sum_i \mu^i_{CALEX} \end{array} \right\} \quad (6)$$

The results can be seen in the Table I shown in FIG. 23. Table I reports the overall LI (first row) and MA (second row) segmentation errors for the AtheroEdge technique. The AtheroEdge process outperformed CALEX in both LI and MA tracings. The average LI segmentation error of the AtheroEdge process was equal to 1.03±0.85 pixels (0.064±0.052 mm), whereas that of the CALEX process was 1.33±0.70 pixels (0.082±0.043 mm). The MA segmentation error for the AtheroEdge process was equal to 1.15±0.83 pixels (0.071±0.051 mm) against 1.78±0.88 pixels (0.110±0.054 mm) for CALEX. Therefore, the AtheroEdge process allowed a reduction of the distal wall segmentation error equal to 22.6% for LI and 35.4% for MA.

FIGS. 16A-16C show sample images from a database of one embodiment.

FIG. 17 shows sample images of the artery recognition phase of Adventitia.

FIG. 18A shows sample images of the de-speckled filter.

FIG. 18B shows sample images of the region of interest (ROI) for an example embodiment.

FIG. 19 shows sample images of the output of the calibration stage of the system of an example embodiment.

FIG. 20 shows the LIMA border segmentation of an example embodiment.

FIG. 21 shows the LI borders with respect to GT borders. In the Figure, the dotted lines are the GT borders while the solid lines are provided by the operation of the various embodiments described herein.

FIG. 22 shows the MA borders with respect to GT borders. In the Figure, the dotted lines are the GT borders while the solid lines are provided by the operation of the various embodiments described herein.

FIG. 23 shows Stage I processing (using automated Artery Recognition Processor). The Figure shows the Far Adventitia using local statistics (CALS).

FIG. 24 shows: A) despeckled image; B) MRAFOAM operator with far adventitia overlaid; C) the region of interest (ROI); and D) CALSFOAM segmentation.

FIG. 25 shows the Stage II output and compared with the GT boundaries (two patients—top row and bottom row).

Though the above system was presented with an automated Artery Recognition system, those of ordinary skill in the art in view of this disclosure will see that other Automated Artery Recognition systems can be used, such as those based on signal processing, where automated far Adventitia is computed followed by the calibration system as described herein. Examples of this are shown in FIGS. 23, 24 and 25.

FIG. 26 is a processing flow diagram illustrating an example embodiment of a computer-implemented system and method for fast, reliable and automated processing for intima-media thickness (IMT) measurements as described herein. The method 2600 of an example embodiment includes: receiving biomedical imaging data and patient demographic data corresponding to a current scan of a patient (processing block 2610); checking the biomedical imaging data in real-time to determine if an artery of the patient has a calcium deposit in a proximal wall of the artery (processing block 2612); acquiring arterial data of the patient as a combination of longitudinal B-mode and transverse B-mode data (processing block 2614); using a data processor to automatically recognize the artery (processing block 2616); using the data processor to calibrate a region of interest around the automatically recognized artery (processing block 2618); and determining the intima-media thickness (IMT) of an arterial wall of the automatically recognized artery (processing block 2620).

Figure 27:
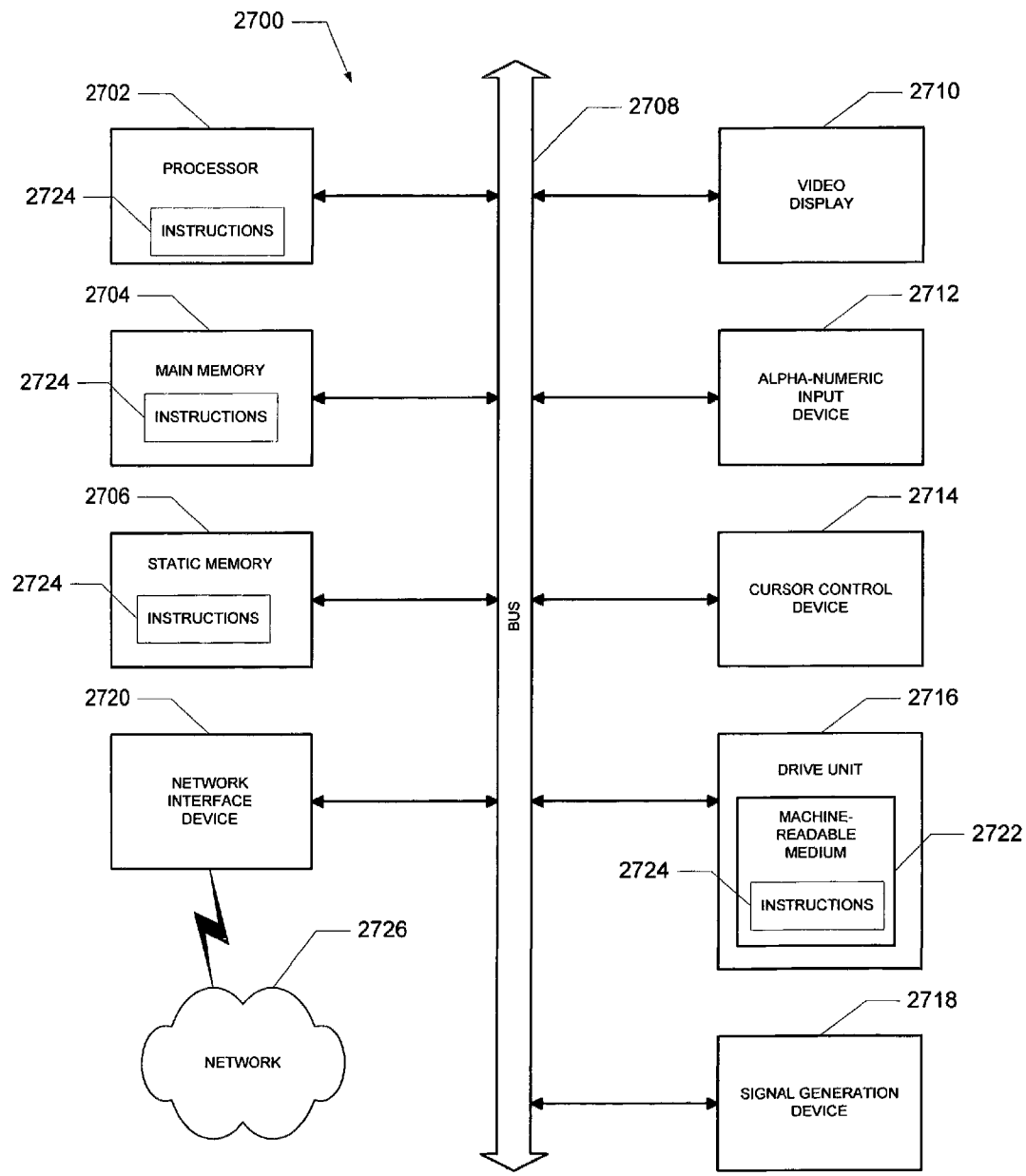
FIG. 27 shows a diagrammatic representation of machine in the example form of a computer system within which a set of instructions when executed may cause the machine to perform any one or more of the methodologies discussed herein.

FIG. 27 shows a diagrammatic representation of machine in the example form of a computer system 2700 within which a set of instructions when executed may cause the machine to perform any one or more of the methodologies discussed herein. In alternative embodiments, the machine operates as a standalone device or may be connected (e.g., networked) to other machines. In a networked deployment, the machine may operate in the capacity of a server or a client machine in server-client network environment, or as a peer machine in a peer-to-peer (or distributed) network environment. The machine may be a personal computer (PC), a tablet PC, a set-top box (STB), a Personal Digital Assistant (PDA), a cellular telephone, a web appliance, a network router, switch or bridge, or any machine capable of executing a set of instructions (sequential or otherwise) that specify actions to be taken by that machine. Further, while only a single machine is illustrated, the term "machine" can also be taken to include any collection of machines that individually or jointly execute a set (or multiple sets) of instructions to perform any one or more of the methodologies discussed herein.

The example computer system 2700 includes a processor 2702 (e.g., a central processing unit (CPU), a graphics processing unit (GPU), or both), a main memory 2704 and a static memory 2706, which communicate with each other via a bus 2708. The computer system 2700 may further include a video display unit 2710 (e.g., a liquid crystal display (LCD) or a cathode ray tube (CRT)). The computer system 2700 also includes an input device 2712 (e.g., a keyboard), a cursor control device 2714 (e.g., a mouse), a disk drive unit 2716, a signal generation device 2718 (e.g., a speaker) and a network interface device 2720.

The disk drive unit 2716 includes a machine-readable medium 2722 on which is stored one or more sets of instructions (e.g., software 2724) embodying any one or more of the methodologies or functions described herein. The instructions 2724 may also reside, completely or at least partially, within the main memory 2704, the static memory 2706, and/or within the processor 2702 during execution thereof by the computer system 2700. The main memory 2704 and the processor 2702 also may constitute machine-readable media. The instructions 2724 may further be transmitted or received over a network 2726 via the network interface device 2720. While the machine-readable medium 2722 is shown in an example embodiment to be a single medium, the term "machine-readable medium" should be taken to include a single medium or multiple media (e.g., a centralized or distributed database, and/or associated caches and servers) that store the one or more sets of instructions. The term "machine-readable medium" can also be taken to include any non-transitory medium that is capable of storing, encoding or carrying a set of instructions for execution by the machine and that cause the machine to perform any one or more of the methodologies of the various embodiments, or that is capable of storing, encoding or carrying data structures utilized by or associated with such a set of instructions. The term "machine-readable medium" can accordingly be taken to include, but not be limited to, solid-state memories, optical media, and magnetic media.

The Abstract of the Disclosure is provided to comply with 37 C.F.R. §1.72(b), requiring an abstract that will allow the reader to quickly ascertain the nature of the technical disclosure. It is submitted with the understanding that it will not be used to interpret or limit the scope or meaning of the claims. In addition, in the foregoing Detailed Description, it can be seen that various features are grouped together in a single embodiment for the purpose of streamlining the disclosure. This method of disclosure is not to be interpreted as reflecting an intention that the claimed embodiments require more features than are expressly recited in each claim. Rather, as the following claims reflect, inventive subject matter lies in less than all features of a single disclosed embodiment. Thus the following claims are hereby incorporated into the Detailed Description, with each claim standing on its own as a separate embodiment.

We claim:

1. A computer-implemented method to correct shadow regions in a current scan of a patient; the method comprising:
   receiving biomedical imaging data and patient demographic, data corresponding to the current scan of a patient;
   checking the biomedical imaging data in real-time to determine if an artery of the patient has a calcium deposit in a proximal wall of the artery;
   acquiring arterial data of the patient as a combination of longitudinal B-mode and transverse B-mode data;

using a data processor to automatically recognize the artery in a distal wall;

using the data processor to calibrate a region of interest around the automatically recognized artery, the region of interest being automatically calibrated;

determining, automatically, the intima-media thickness (IMT) of an arterial wall of the automatically recognized artery; and using the data processor to correct the IMT in the shadow regions in longitudinal B-mode ultrasound images by use of information from transverse B-mode ultrasound images.

2. The method as claimed in claim 1 wherein the method is applied for automated recognition using a multi-resolution approach.

3. The method as claimed in claim 1 wherein the method is applied for automated recognition using a multi-resolution approach, where borders of the arterial wall are determined in coarse resolution.

4. The method as claimed in claim 1 wherein the method is applied for automated recognition using a multi-resolution approach, where borders of the arterial wall are determined in coarse resolution and up-sampled back onto an original high resolution image.

5. The method as claimed in claim 1 including reducing speckle in real time in the region where the automated artery is recognized.

6. The method as claimed in claim 1 including computing a coarse resolution by convolution of higher order derivative of Gaussian kernels.

7. The method as claimed in claim 1 including computing a coarse resolution by convolution of higher order derivative of Gaussian kernels with and without calcium present in the arterial proximal wall.

8. The method as claimed in claim 1 wherein the automated recognition is implemented using a feature based method, where the IMT is used as a scale in the higher order derivative of Gaussian Kernel in multi-resolution framework.

9. The method as claimed in claim 1 wherein the calibration of the region is guided by the automated recognition of the artery using higher order derivatives of Gaussian kernels, where a scale is empirically modeled as IMT thickness.

10. The method as claimed in claim 1 wherein the calibration of the region uses a Derivative of Gaussian (DoG) image convolved with a Gaussian Kernel in the region guided by an automated recognition system which is a multi-resolution approach, using higher order derivatives.

11. The method as claimed in claim 10 including applying a DoG filter to a speckle-free region of interest on the original image as guided by the automated recognition of the artery.

12. The method as claimed in claim 1 including determining the IMT based in part on the patient's ethnicity, demographics, age, and gender.

13. The method as claimed in claim 1 including computing peaks in the calibration phase.

14. The method as claimed in claim 1 wherein the calibration used is a classifier, a deformable model, a edge detector, or a combination of an edge detector with deformable model.

\* \* \* \* \*